US008586735B2

(12) United States Patent
Vogel et al.

(10) Patent No.: US 8,586,735 B2
(45) Date of Patent: Nov. 19, 2013

(54) HYDROXYPHENYL TRIAZINES WITH AN AROMATIC CARBOCYCLIC FUSED RING SYSTEM

(71) Applicant: Ciba Specialty Chemicals Holding Inc., Basel (CH)

(72) Inventors: Thomas Vogel, Haltigen (DE); Adalbert Braig, Binzen (DE); Thomas Schafer, Liestal (DE); Rachel Kohli Steck, Basel (CH); Valerie Stutz, Munchenstein (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/747,706

(22) Filed: Jan. 23, 2013

(65) Prior Publication Data

US 2013/0143051 A1    Jun. 6, 2013

Related U.S. Application Data

(62) Division of application No. 11/921,605, filed as application No. PCT/EP2006/062750 on May 31, 2006, now Pat. No. 8,389,719.

(30) Foreign Application Priority Data

Oct. 6, 2005   (EP) ..................................... 01505104

(51) Int. Cl.
  *C07D 251/00*   (2006.01)
  *C08G 73/06*   (2006.01)

(52) U.S. Cl.
  USPC ........................... 544/216; 544/180; 524/100

(58) Field of Classification Search
  USPC ................... 544/216, 180; 524/100
  See application file for complete search history.

(56) References Cited

U.S. PATENT DOCUMENTS

| 5,354,794 A | 10/1994 | Stevenson et al. |
| 5,476,937 A | 12/1995 | Stevenson et al. |
| 5,556,973 A | 9/1996 | Stevenson et al. |
| 5,672,704 A | 9/1997 | Toan et al. |
| 5,990,188 A | 11/1999 | Patel et al. |

FOREIGN PATENT DOCUMENTS

| CH | GB 1107143 | * | 3/1968 |
| GB | 1107143 | | 3/1968 |
| JP | 8-53427 | | 2/1996 |
| JP | 8-506608 | | 7/1996 |
| JP | 8-259545 | | 10/1996 |
| JP | 10-183016 | | 7/1998 |
| JP | 11-71356 | | 3/1999 |
| JP | 2000-305715 | | 11/2000 |
| JP | 2002-524452 | | 8/2002 |
| JP | 2002-529538 | | 9/2002 |
| WO | 9418278 | | 8/1994 |
| WO | 0014077 | | 3/2000 |
| WO | 00/29392 | | 5/2000 |
| WO | 0029392 | | 5/2000 |
| WO | WO 00/29392 | * | 5/2000 |

OTHER PUBLICATIONS

Yamada et al; Touch panel in liquid crystal display; Nov. 2000; Sharp Corp., Chem Abstract 133: 357343.*
English language abstract of JP 11-71356 (Mar. 16, 1999).
International Search Report received for International Application No. PCT/EP2006/062750, mailed on Jan. 8, 2006, 3 pages.

* cited by examiner

*Primary Examiner* — Duc Truong
(74) *Attorney, Agent, or Firm* — Shruti Costales

(57) ABSTRACT

The instant invention relates to novel hydroxyphenyl triazine UV-absorbers with an aromatic carbocyclic fused ring system having a long wavelength shifted absorption spectrum with significant absorbance up to 420 nm. Further aspects of the invention are a process for their preparation, a UV stabilized composition containing the new UV-absorbers, a process for the stabilization of organic materials and the use of the new compounds as UV-light stabilizers for organic materials.

19 Claims, No Drawings

HYDROXYPHENYL TRIAZINES WITH AN AROMATIC CARBOCYCLIC FUSED RING SYSTEM

This application is a DIV of Ser. No. 11/921,605 filed Dec. 5, 2007 now U.S. Pat. No. 8,389,719
Which is a 371 of PCT/EP/2006/062750 FILED May 31, 2006.

The instant invention relates to novel hydroxyphenyl triazine UV-absorbers having a long wavelength shifted absorption spectrum with significant absorbance up to 420 nm. Further aspects of the invention are a process for their preparation, a UV stabilized composition containing the new UV-absorbers, a process for the stabilization of organic materials and the use of the new compounds as UV-light stabilizers for organic materials.

Polymeric substrates containing aromatic moieties, such as for example adhesives or coating resins based on aromatic epoxides, aromatic polyesters or aromatic (poly-) isocyanates are highly sensitive to UV/VIS radiation up to wavelengths of approximately 420 nm.

The protection of such adhesive or coating layers with a UV absorbing layer on top is extremely difficult, since already very small amounts of radiation—even in the range of around 410 nm—penetrating the UV absorbing top coating are sufficient to cause delamination and peeling off of the protective coating.

Typical applications, in which long wavelength shifted UV absorbers are extremely useful, are automotive coatings.

Today's automotive coatings have applied an anticorrosive cathodic electro coat directly on the steel plate. Due to the significantly red shifted light sensitivity of the cathodic resins (up to approximately 400-420 nm) it is not possible to protect the cathodic electro coat with conventional prior art UV-absorbers in the top coatings adequately.

In order to better protect such sensitive layers, attempts have been made to shift the UV absorption of triazines towards longer wavelengths. For example, U.S. Pat. Nos. 5,354,794, 5,476,937 and 5,556,973 describe red-shifted hydroxyphenyl triazines.

However, the instant compounds may absorb a greater amount of light up to 420-450 nm, in particular up to 420 nm, than the state of the art. The compounds remain unexpectedly photochemically stable and show virtually no migration in typical coating applications.

An aspect of the invention is a compound of formula (I)

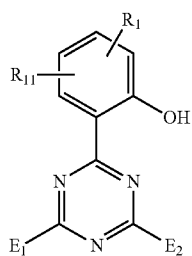

(I)

wherein
$E_1$ is a substituted or unsubstituted aromatic carbocyclic fused ring system comprising at least 3 rings;
$E_2$ is independently as defined for $E_1$; or is a substituted or unsubstituted naphthyl; or is a substituted or unsubstituted aromatic hetero ring system comprising one or more rings; or corresponds to the formula

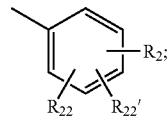

$R_1$ is H, $C_1$-$C_{24}$alkyl, $C_2$-$C_{18}$alkenyl, $C_5$-$C_{12}$cycloalkyl, $C_7$-$C_{15}$phenylalkyl, phenyl, or said phenyl or said phenylalkyl substituted on the phenyl ring by $C_1$-$C_8$alkyl; or $OR_3$;

$R_2$ is H, $C_1$-$C_{18}$alkyl; $C_2$-$C_6$alkenyl; phenyl; phenyl substituted by $C_1$-$C_8$alkyl or by $C_1$-$C_8$alkoxy; $C_7$-$C_{11}$phenylalkyl; $C_5$-$C_{12}$cycloalkyl; $COOR_4$; CN; $NH_2$, $NHR_7$, —N($R_7$)($R_8$), NH—CO—$R_5$; halogen; $C_1$-$C_{18}$haloalkyl; $C_1$-$C_{18}$alkoxy; —S—$R_3$ or —O—$R_3$;

$R_3$ is independently H, $C_1$-$C_{18}$alkyl; $C_5$-$C_{12}$cycloalkyl; $C_3$-$C_{18}$alkenyl; phenyl; $C_1$-$C_{18}$alkyl that is substituted by phenyl, OH, $C_1$-$C_{18}$alkoxy, $C_5$-$C_{12}$cycloalkoxy, $C_3$-$C_{18}$alkenyloxy, halogen, —COOH, —COOR$_4$, —O—CO—$R_5$, —O—CO—O—$R_6$, —CO—$NH_2$, —CO—NHR$_7$, —CO—N($R_7$)($R_8$), CN, $NH_2$, $NHR_7$, —N($R_7$)($R_8$), —NH—CO—$R_5$, phenoxy, $C_1$-$C_{18}$alkyl-substituted phenoxy, phenyl-$C_1$-$C_4$-alkoxy, $C_6$-$C_{15}$bicycloalkoxy, $C_6$-$C_{15}$bicycloalkyl-alkoxy, $C_6$-$C_{15}$bicycloalkenyl-alkoxy and/or by $C_6$-$C_{15}$tricycloalkoxy; $C_5$-$C_{12}$cycloalkyl that is substituted by OH, $C_1$-$C_4$alkyl, $C_2$-$C_6$alkenyl and/or by —O—CO—$R_5$; —CO—$R_9$ or —SO$_2$—$R_{10}$; or $C_3$-$C_{50}$alkyl that is interrupted by one or more oxygen atoms and is unsubstituted or substituted by OH, phenoxy and/or by $C_7$-$C_{18}$alkylphenoxy; or -A; —$CH_2$—CH(XA)-$CH_2$—O—$R_{12}$; —$CR_{13}R_{13}'$—($CH_2$)$_m$—X-A; —$CH_2$—CH(OA)-$R_{14}$; —$CH_2$—CH(OH)—$CH_2$—XA;

—$CR_{15}R_{15}'$—C(=$CH_2$)—$R_{15}''$; —$CR_{13}R_{13}'$—($CH_2$)$_m$—CO—X-A; —$CR_{13}R_{13}'$—($CH_2$)$_m$—CO—O—$CR_{15}R_{15}'$—C(=$CH_2$)—$R_{15}''$ or —CO—O—$CR_{15}R_{15}'$—C(=$CH_2$)—$R_{15}''$;

A is —CO—$CR_{16}$=CH—$R_{17}$;

$R_4$ is independently $C_1$-$C_{18}$alkyl; $C_3$-$C_{18}$alkenyl; $C_7$-$C_{11}$phenylalkyl; $C_5$-$C_{12}$cycloalkyl; or $C_3$-$C_{50}$alkyl that is interrupted by one or more of —O—, —NH—, —NR$_7$— and —S— and is unsubstituted or substituted by OH, phenoxy and/or by $C_7$-$C_{18}$alkylphenoxy; or $C_2$-$C_{12}$hydroxyalkyl;

$R_5$ is independently H; $C_1$-$C_{18}$alkyl; $C_1$-$C_{18}$alkyl substituted by COOH or by COOR$_4$; $C_2$-$C_{18}$alkenyl; $C_2$-$C_{18}$alkenyl substituted by COOH or by COOR$_4$; $C_5$-$C_{12}$cycloalkyl; phenyl; $C_7$-$C_{11}$phenylalkyl; $C_6$-$C_{15}$bicycloalkyl; $C_6$-$C_{15}$bicycloalkenyl; or $C_6$-$C_{15}$tricycloalkyl;

$R_6$ is independently $C_1$-$C_{18}$alkyl; $C_3$-$C_{18}$alkenyl; phenyl; $C_7$-$C_{11}$phenylalkyl; or $C_5$-$C_{12}$cycloalkyl;

$R_7$ and $R_8$ are independently $C_1$-$C_{12}$alkyl; $C_3$-$C_{12}$alkoxyalkyl; $C_4$-$C_{16}$dialkylaminoalkyl; or $C_5$-$C_{12}$cycloalkyl; or together form $C_3$-$C_9$-alkylene, -oxaalkylene or -azaalkylene;

$R_9$ is independently $C_1$-$C_{15}$alkyl; $C_2$-$C_{15}$alkenyl; phenyl; $C_5$-$C_{12}$cycloalkyl; $C_7$-$C_{11}$phenylalkyl; $C_6$-$C_{15}$bicycloalkyl, $C_6$-$C_{15}$bicycloalkyl-alkyl, $C_6$-$C_{15}$bicycloalkenyl, or $C_6$-$C_{15}$tricycloalkyl;

$R_{10}$ is independently $C_1$-$C_{12}$alkyl; phenyl; naphthyl or $C_7$-$C_{14}$alkylphenyl;

$R_{11}$ and $R_{22}$ are independently H; $C_1$-$C_{18}$alkyl; $C_3$-$C_6$alkenyl; $C_5$-$C_{12}$cycloalkyl; phenyl; naphthyl; biphenylyl; $C_7$-$C_{11}$phenylalkyl; $C_7$-$C_{14}$alkylphenyl; halogen; $C_1$-$C_{18}$haloalkyl; or $C_1$-$C_{18}$alkoxy;

$R_{12}$ is independently $C_1$-$C_{18}$alkyl; $C_3$-$C_{18}$alkenyl; phenyl; phenyl substituted by one to three of the radicals $C_1$-$C_8$alkyl, $C_1$-$C_8$alkoxy, $C_3$-$C_8$alkenyloxy, halogen and trifluoromethyl; $C_7$-$C_{11}$-phenylalkyl; $C_5$-$C_{12}$cycloalkyl; $C_6$-$C_{15}$tricycloalkyl; $C_6$-$C_{15}$bicycloalkyl; $C_6$-$C_{15}$bicycloalkyl-alkyl; $C_6$-$C_{15}$bicycloalkenyl-alkyl; —CO—$R_5$; or $C_3$-$C_{50}$alkyl that is interrupted by one or more of —O—, —NH—, —$NR_7$— and —S— and is unsubstituted or substituted by OH, phenoxy and/or by $C_7$-$C_{18}$alkylphenoxy;

$R_{13}$ and $R_{13}'$ are independently H; $C_1$-$C_{18}$alkyl; or phenyl;

$R_{14}$ is independently $C_1$-$C_{18}$alkyl; $C_3$-$C_{12}$alkoxyalkyl; phenyl; or phenyl-$C_1$-$C_4$alkyl;

$R_{15}$, $R_{15}'$ and $R_{15}''$ are independently H or $CH_3$;

$R_{16}$ is independently H; —$CH_2$—COO—$R_4$; $C_1$-$C_4$alkyl; or CN;

$R_{17}$ is independently H; —COO$R_4$; $C_1$-$C_{17}$alkyl; or phenyl;

$R_{22}'$ has one of the meanings of $R_{11}$; or is $NH_2$, $NHR_7$, NH—CO—$R_5$; —S—$R_3$, —N($R_7$)($R_5$) or O$R_3$;

X is independently —NH—; —$NR_7$—; —O—; —NH—$(CH_2)_p$—NH—; or —O—$(CH_2)_q$—NH—;

and the indices are as follows:

m is a number from 0 to 19;
n is a number from 1 to 8;
p is a number from 0 to 4; and
q is a number from 2 to 4.

Preferably $R_{11}$ and $R_{22}$ are H.

Of interest is $R_{22}'$ that is O$R_3$, especially OH.

For instance, $E_2$ is independently as defined for $E_1$; or corresponds to the formula

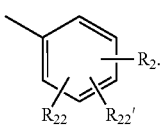

Substituents at the aromatic carbocyclic fused ring system comprising at least 3 rings or at naphthyl or at aromatic hetero ring system comprising one or more rings are, for example, independently of one another one or more radicals as defined for $R_{22}$ and $R_{22}'$.

Examples of aromatic carbocyclic fused ring systems comprising at least 3 rings are radicals of anthracene, phenanthrene, fluoranthene, pyrene, chrysene, benzanthracene, dibenzanthracene, benzofluoranthene, benzopyrene, indenopyrene and benzoperlyene, preferably phenanthrene, fluoranthene and pyrene, most preferably fluoranthene and pyrene.

For instance, an aromatic carbocyclic fused ring system comprising at least 3 rings means that this ring system comprises at least 3 aromatic rings, in particular at least three aromatic fused rings.

Examples of aromatic hetero ring systems comprising one or more rings are thienyl, benzo[b]thienyl, naphtho[2,3-b]thienyl, thianthrenyl, furyl, benzofuryl, isobenzofuryl, dibenzofuryl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl.

For instance, there is not more than one group $R_3$ per molecule that is selected from the group consisting of -A; —$CH_2$—CH(XA)-$CH_2$—O—$R_{12}$; —$CR_{13}R_{13}'$—$(CH_2)_m$—X-A; —$CH_2$—CH(OA)-$R_{14}$; —$CH_2$—CH(OH)—$CH_2$—XA;

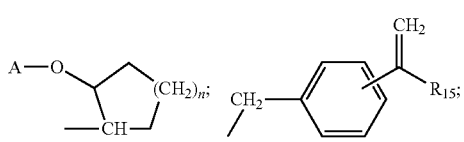

—$CR_{15}R_{15}'$—C(=$CH_2$)—$R_{15}''$; —$CR_{13}R_{13}'$—$(CH_2)_m$—CO—X-A; —$CR_{13}R_{13}'$—$(CH_2)_m$—CO—O—$CR_{15}R_{15}'$—C(=$CH_2$)—$R_{15}''$ and —CO—O—$CR_{15}R_{15}'$—C(=$CH_2$)—$R_{15}''$.

Compounds of formula (I) containing a group -A; —$CH_2$—CH(XA)-$CH_2$—O—$R_{12}$; —$CR_{13}R_{13}'$—$(CH_2)_m$—X-A; —$CH_2$—CH(OA)-$R_{14}$; —$CH_2$—CH(OH)—$CH_2$—XA;

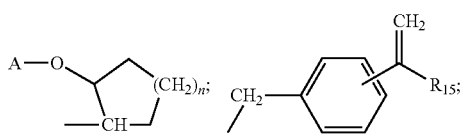

—$CR_{15}R_{15}'$—C(=$CH_2$)—$R_{15}''$; —$CR_{13}R_{13}'$—$(CH_2)_m$—CO—X-A; —$CR_{13}R_{13}'$—$(CH_2)_m$—CO—O—$CR_{15}R_{15}'$—C(=$CH_2$)—$R_{15}''$ or —CO—O—$CR_{15}R_{15}'$—C(=$CH_2$)—$R_{15}''$ may be copolymerized into various polymeric substrates such as listed under polymers below.

Within the scope of the definitions given, alkyl are branched or unbranched alkyl, e.g. methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl.

For example $C_5$-$C_{12}$cycloalkyl include cyclopentyl, cyclohexyl, cycloheptyl, cyclooctyl, cyclononyl, cyclodecyl, cycloundecyl and cyclodocecyl. Cyclopentyl, cyclohexyl, cyclooctyl and cyclododecyl are preferred.

Alkenyl include, within the scope of the definitions given, inter alia allyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl and n-octadec-4-enyl.

Substituted alkyl, cycloalkyl or phenyl radicals may be mono- or poly-substituted and may carry substituents at the binding carbon atom (in the α-position) or at other carbon atoms; if a substituent is bonded by a hetero atom (such as e.g. alkoxy), it is preferably not in the α-position and the substituted alkyl radical comprises 2, especially 3, or more carbon atoms. A plurality of substituents is preferably bonded to different carbon atoms.

Alkyl interrupted by —O—, —NH—, —NR$_7$— and/or by —S— may be interrupted by one or more of the mentioned groups, in each case normally one group being inserted into a bond and heterohetero bonds, such as, for example, O—O, S—S, NH—NH etc. not occurring; if the interrupted alkyl is, in addition, substituted, the substituents are not normally in the α-position with respect to the hetero atom. If a plurality of interrupting groups of the type —O—, —NH—, —NR$_7$— and —S— occurs in a radical, those groups are usually identical.

Hydroxyalkyl means an alkyl group substituted by hydroxy.

For instance alkoxy, phenoxy, alkenyloxy and cycloalkoxy mean the group OZ, wherein Z is alkyl, phenyl, alkenyl and cycloalkyl respectively.

Phenylalkyl comprises within the limits of carbon atoms given, for example, benzyl, α-methylbenzyl, phenylethyl, phenylpropyl, phenylbutyl, phenylpentyl and phenylhexyl; whereby benzyl, α-methyl benzyl and α,α-dimethylbenzyl are preferred.

Alkylphenyl and alkylphenoxy are alkyl-substituted phenyl and phenoxy, respectively.

A halogen substituent is —F, —Cl, —Br or —I; —F or —Cl, and especially —Cl, is preferred. Haloalkyl is especially chloroalkyl or trifluoromethyl; trifluoromethyl is of particular importance industrially.

Alkylene is e.g. methylene, ethylene, propylene, butylene, pentylene, hexylene, etc. The alkyl chain may also be branched in that case, such as e.g. in isopropylene.

$C_4$-$C_{12}$Cycloalkenyl is e.g. 2-cyclobuten-1-yl, 2-cyclopenten-1-yl, 2,4-cyclopentadien-1-yl, 2-cyclohexen-1-yl, 2-cyclohepten-1-yl or 2-cycloocten-1-yl.

$C_6$-$C_{15}$Bicycloalkyl is e.g. bornyl, norbornyl or 2.2.2-bicyclooctyl. Bornyl and norbornyl, and especially bornyl and norborn-2-yl, are preferred.

$C_6$-$C_{15}$Bicycloalkoxy is, for example, bornyloxy or norborn-2-yl-oxy.

$C_6$-$C_{15}$Bicycloalkyl-alkyl or -alkoxy is alkyl or alkoxy substituted by bicycloalkyl, the total number of carbon atoms being 6-15; examples are norbornane-2-methyl and norbornane-2-methoxy.

$C_6$-$C_{15}$Bicycloalkenyl is e.g. norbornenyl or norbornadienyl. Norbornenyl, and especially norborn-5-enyl, is preferred.

$C_6$-$C_{15}$Bicycloalkenyl-alkoxy is alkoxy substituted by bicycloalkenyl, the total number of carbon atoms being 6-15; an example is norborn-5-enyl-2-methoxy.

$C_6$-$C_{15}$Tricycloalkyl is e.g. 1-adamantyl or 2-adamantyl; 1-adamantyl is preferred.

$C_6$-$C_{15}$Tricycloalkoxy is e.g. adamantyloxy.

$C_3$-$C_{12}$Heteroaryl is preferably pyridinyl, pyrimidinyl, triazinyl, pyrrolyl, furanyl, thiophenyl or quinolinyl.

The compounds of formula (I) and their starting materials can be prepared by methods known in the art. For example, the compounds of formula (I) are prepared by Friedel-Crafts addition of halotriazines to corresponding aromatic compounds and phenols analogously to one of the methods specified in EP-A-434 608 or in one of the publications mentioned at the beginning or analogously to one of the methods specified in the publication by H. Brunetti and C. E. Lüthi, Helv. Chim. Acta 55, 1566 (1972); see also U.S. Pat. Nos. 5,726, 310, 6,057,444, 6,225,468, and EP-A-941 989, WO 00/29392. That procedure can be followed by a further reaction according to known methods; such reactions and processes are described, for example, in EP-A-434 608.

To prepare the compounds of formula (I), advantageously one equivalent of cyanuric chloride is used as starting material and is reacted with approximately one equivalent each of an unsubstituted or substituted aromatic carbocyclic fused ring system comprising at least three rings, a further aromatic compound and a phenol, such as, for example, resorcinol. Suitable aromatic starting materials must have at least one C—H bond on the aromatic compound; the phenol used must contain an ortho-position unsubstituted in that manner. The further aromatic compound may be a naphthalene, an aromatic hetero ring system or a benzene, each of which are substituted or unsubstituted, or the same or another unsubstituted or substituted aromatic carbocyclic fused ring system comprising at least three rings.

The reaction is carried out in a manner known per se by reacting the starting materials with the cyanuric halide in an inert solvent in the presence of anhydrous $AlCl_3$. Aluminium trichloride can be used in excess and/or in admixture with HCl, for example conc. aqu. hydrochloric acid. Advantageously, the aromatic carbocyclic fused ring system is reacted first and the phenol compound is added last.

The reaction product of cyanuric halide and aromatic carbocyclic fused ring system can be further reacted directly or can also be isolated in known manner.

Suitable solvents are, for example, hydrocarbons, chlorinated hydrocarbons, hydrocarbons containing SO or $SO_2$ groups, or nitrated aromatic hydrocarbons; especially aromatic hydrocarbons, chlorinated or nitrated aromatic hydrocarbons.

The temperature is generally not critical; the temperatures used are usually from −20° C. to the boiling point of the solvent, for example from 0° C. to 130° C.

Free phenolic hydroxyl groups of the reaction product in the p-position with respect to the triazine ring can be further modified in known manner, for example etherified. Working-up can be carried out by customary methods, e.g. by extraction and separation steps, filtration and drying; if necessary, further purification steps can be performed, e.g. recrystallisation.

The products from the above-described reactions can be further modified within the scope of the definitions given for formula (I) according to known methods.

The reactions can be carried out with the exclusion of oxygen, for example by flushing with an inert gas, such as argon; oxygen is not troublesome in every case, however, and therefore the reaction can also be carried out without the mentioned measure. When the reaction is complete, working-up can be carried out according to customary methods.

Of interest is a compound, wherein $E_1$ is the formula

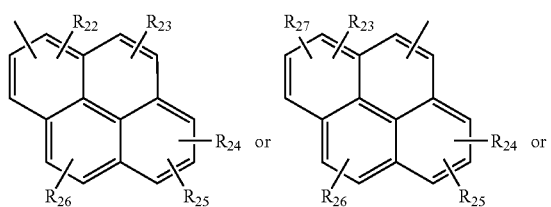

-continued

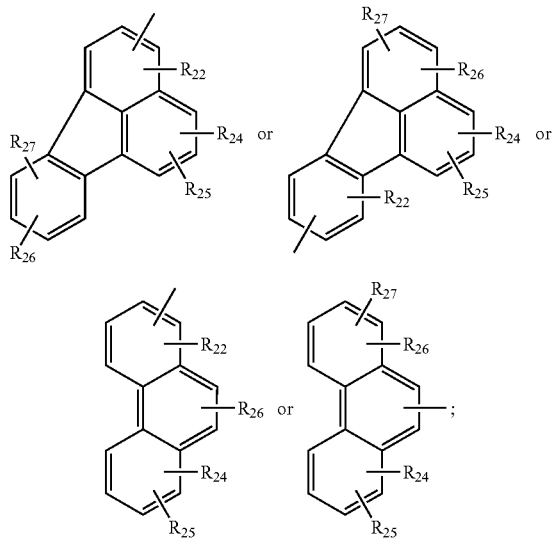

$E_2$ is independently as defined for $E_1$ or corresponds to the formula

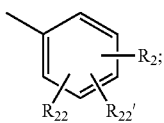

$R_{25}$ and $R_{27}$ are independently as defined for $R_{22}$;
$R_{23}$, $R_{24}$ and $R_{26}$ are independently as defined for $R_{22}'$;
and the other groups are as defined above.

For example, $E_1$ is not of formula

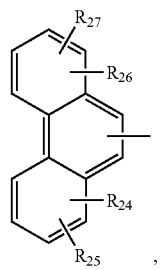

especially not of formula

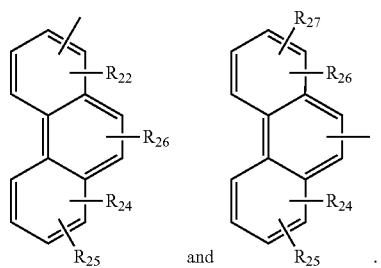

For instance,
$R_2$ is H, $C_1$-$C_{18}$alkyl; $C_2$-$C_6$alkenyl; phenyl; phenyl substituted by $C_1$-$C_8$alkyl or by $C_1$-$C_8$alkoxy; NH—CO—$R_5$; halogen; $C_1$-$C_{18}$haloalkyl; $C_1$-$C_{18}$alkoxy; or $OR_3$;
$R_{22}$, $R_{25}$ and $R_{27}$ are independently H, $C_7$-$C_{11}$phenylalkyl or $C_1$-$C_8$alkyl;
$R_{22}'$, $R_{23}$, $R_{24}$ and $R_{26}$ are independently H; $C_1$-$C_8$alkyl; $C_3$-$C_6$alkenyl; $C_7$-$C_{11}$phenylalkyl; $C_5$-$C_{12}$cycloalkyl; phenyl; naphthyl; biphenylyl; $C_7$-$C_{14}$alkylphenyl; $NHR_7$; —$N(R_7)(R_8)$; halogen; $C_1$-$C_{18}$haloalkyl; or $OR_3$.

For example,
$R_2$ is H, $C_1$-$C_8$alkyl; phenyl; phenyl substituted by methyl or by methoxy; NH—CO—$R_5$; trifluoromethyl; $C_1$-$C_{18}$alkoxy; or $OR_3$;
$R_{22}$, $R_{25}$ and $R_{27}$ are independently H, $C_7$-$C_{11}$phenylalkyl or $C_1$-$C_8$alkyl;
$R_{22}'$, $R_{23}$, $R_{24}$ and $R_{26}$ are independently H; $C_1$-$C_8$alkyl; $C_3$-$C_6$alkenyl; $C_7$-$C_{11}$phenylalkyl; $C_5$-$C_{12}$cycloalkyl; trifluoromethyl; phenyl; naphthyl; biphenylyl; $C_7$-$C_{14}$alkylphenyl; $NHR_7$; —$N(R_2)(R_8)$; or $OR_3$.

Preferably, $R_{23}$, $R_{24}$, $R_{25}$, $R_{26}$ and $R_{27}$ are H. Of interest is $R_{22}$ that is H.

Of further interest is a compound, wherein
$R_1$ is H or $C_1$-$C_{24}$alkyl, $C_2$-$C_{18}$alkenyl, $C_5$-$C_{12}$cycloalkyl, $C_7$-$C_{15}$phenylalkyl, phenyl, or said phenyl or said phenylalkyl substituted on the phenyl ring by $C_1$-$C_8$alkyl; or $OR_3$;
$R_2$ is H, $C_1$-$C_{18}$alkyl; $C_2$-$C_6$alkenyl; phenyl; phenyl substituted by $C_1$-$C_8$alkyl or by $C_1$-$C_8$alkoxy; NH—CO—$R_5$; halogen; $C_1$-$C_{18}$haloalkyl; $C_1$-$C_{18}$alkoxy; or $OR_3$;
$R_3$ is independently H, $C_1$-$C_{18}$alkyl; $C_5$-$C_{12}$cycloalkyl; $C_3$-$C_{18}$alkenyl; phenyl; $C_1$-$C_{18}$alkyl that is substituted by phenyl, OH, $C_1$-$C_{18}$alkoxy, $C_5$-$C_{12}$cycloalkoxy, $C_3$-$C_{18}$alkenyloxy, halogen, —COOH, —COO$R_4$, —O—CO—$R_5$, —O—CO—O—$R_6$, —CO—$NH_2$, —CO—$NHR_7$, —CO—$N(R_7)(R_8)$, CN, $NH_2$, $NHR_7$, —$N(R_7)(R_8)$, —NH—CO—$R_5$, phenoxy, $C_1$-$C_{18}$alkyl-substituted phenoxy and/or by phenyl-$C_1$-$C_4$alkoxy; $C_5$-$C_{12}$cycloalkyl that is substituted by OH, $C_1$-$C_4$alkyl, $C_2$-$C_6$alkenyl and/or by —O—CO—$R_5$; or —$SO_2$—$R_{10}$; or $C_3$-$C_{50}$alkyl that is interrupted by one or more oxygen atoms and is unsubstituted or substituted by OH, phenoxy and/or by $C_7$-$C_{18}$alkylphenoxy; or —CO—CH=$CH_2$ or —CO—C($CH_3$)=$CH_2$;
$R_4$ is independently $C_1$-$C_{18}$alkyl; $C_3$-$C_{18}$alkenyl; $C_7$-$C_{11}$phenylalkyl; $C_5$-$C_{12}$cycloalkyl; or $C_3$-$C_{50}$alkyl that is interrupted by one or more of —O—, —NH—, —$NR_7$— and —S— and is unsubstituted or substituted by OH, phenoxy and/or by $C_7$-$C_{18}$alkylphenoxy; or $C_2$-$C_{12}$hydroxyalkyl;
$R_5$ is independently H; $C_1$-$C_{18}$alkyl; $C_2$-$C_{16}$alkenyl; $C_5$-$C_{12}$cycloalkyl; phenyl; or $C_7$-$C_{11}$phenylalkyl;
$R_6$ is independently $C_1$-$C_{18}$alkyl; $C_3$-$C_{18}$alkenyl; phenyl; $C_7$-$C_{11}$phenylalkyl; or $C_5$-$C_{12}$cycloalkyl;
$R_7$ and $R_8$ are independently $C_1$-$C_{12}$alkyl; $C_3$-$C_{12}$alkoxyalkyl; $C_4$-$C_{16}$dialkylaminoalkyl; or cyclohexyl; or together form $C_3$-$C_9$-alkylene or -oxaalkylene;
$R_{10}$ is independently $C_1$-$C_{12}$alkyl; phenyl; naphthyl or $C_7$-$C_{14}$alkylphenyl;
$R_{11}$ and $R_{22}$ are independently H, $C_7$-$C_{11}$phenylalkyl or $C_1$-$C_8$alkyl;
$R_{22}'$ is independently H; $C_1$-$C_8$alkyl; $C_3$-$C_6$alkenyl; $C_7$-$C_{11}$phenylalkyl; $C_5$-$C_{12}$cycloalkyl; phenyl; naphthyl; biphenylyl; $C_7$-$C_{14}$alkylphenyl; $NHR_7$; —$N(R_7)(R_8)$; halogen; $C_1$-$C_{18}$haloalkyl; or $OR_3$;
and the other groups are as defined above.

Also of interest is a compound, wherein
$R_1$ is H or $C_1$-$C_{24}$alkyl, $C_2$-$C_{18}$alkenyl, $C_5$-$C_{12}$cycloalkyl, $C_7$-$C_{15}$phenylalkyl, phenyl, or said phenyl or said phenylalkyl substituted on the phenyl ring by $C_1$-$C_8$alkyl; or $OR_3$;
$R_2$ is H, $C_1$-$C_8$alkyl; phenyl; phenyl substituted by methyl or by methoxy; NH—CO—$R_5$; trifluoromethyl; $C_1$-$C_{18}$alkoxy; or $OR_3$;
$R_3$ is independently H, $C_1$-$C_{18}$alkyl; cyclohexyl; $C_3$-$C_{18}$alkenyl; $C_1$-$C_{18}$alkyl that is substituted by phenyl, OH, $C_1$-$C_{18}$alkoxy, cyclohexyloxy, halogen, —COOH, —COOR$_4$, —O—CO—R$_5$, —CO—NHR$_7$, —CO—N(R$_7$)(R$_9$), CN, NHR$_7$, —N(R$_7$)(R$_5$), —NH—CO—R$_5$ and/or by phenyl-$C_1$-$C_4$alkoxy; or cyclohexyl that is substituted by OH, $C_1$-$C_4$alkyl, $C_2$-$C_6$alkenyl and/or by —O—CO—R$_5$;
$R_4$ is independently $C_1$-$C_{18}$alkyl; $C_7$-$C_{11}$phenylalkyl; $C_5$-$C_{12}$cycloalkyl; or $C_2$-$C_{12}$hydroxyalkyl;
$R_5$ is independently H; $C_1$-$C_{18}$alkyl; $C_2$-$C_8$alkenyl; cyclohexyl; phenyl; or $C_7$-$C_{11}$phenylalkyl;
$R_7$ and $R_8$ are independently $C_3$-$C_{12}$alkyl or cyclohexyl; or together form $C_3$-$C_9$oxaalkylene;
$R_{11}$ and $R_{22}$ are independently H, $C_7$-$C_{11}$phenylalkyl or $C_1$-$C_8$alkyl;
$R_{22}'$ is independently H; $C_1$-$C_8$alkyl; $C_3$-$C_6$alkenyl; $C_7$-$C_{11}$phenylalkyl; $C_5$-$C_{12}$cycloalkyl; trifluoromethyl; phenyl; naphthyl; biphenylyl; $C_7$-$C_{14}$alkylphenyl; NHR$_7$; —N(R$_7$)(R$_9$); or OR$_3$;
and the other groups are as defined above.

Preferred is a compound corresponding to formula (II)

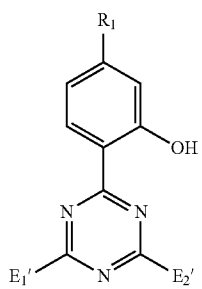

wherein
$E_1'$ is the formula

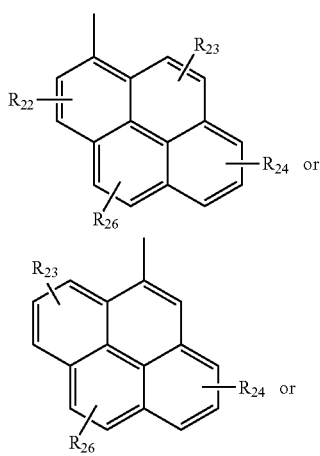

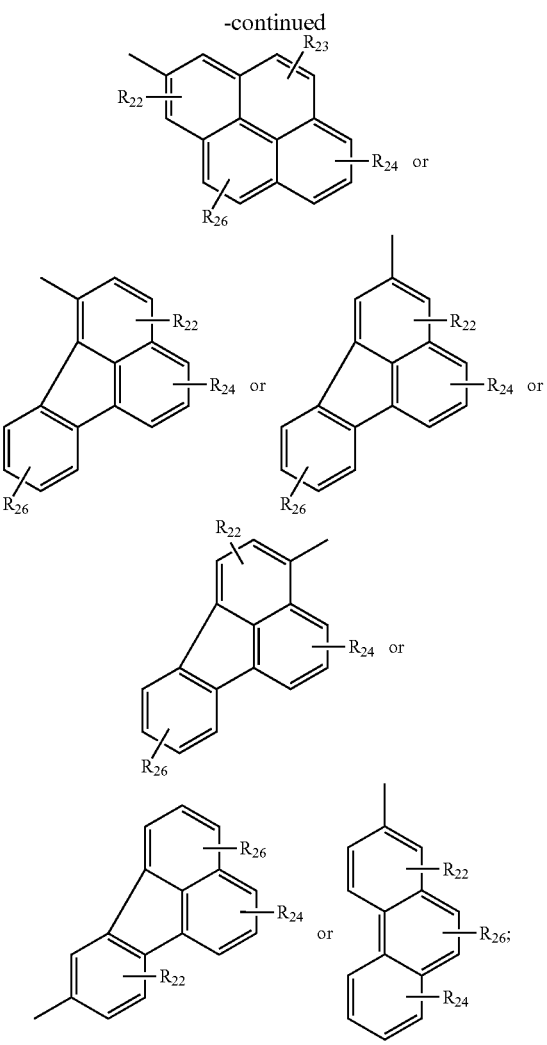

$E_2'$ is independently as defined for $E_1'$ or corresponds to the formula

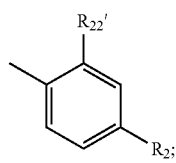

and the other groups are as defined above.
More preferred is a compound wherein
$E_1'$ is the formula

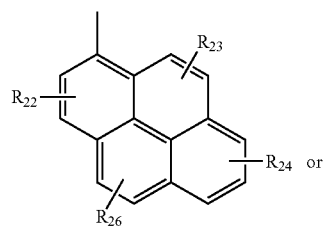

-continued

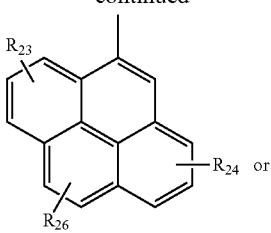

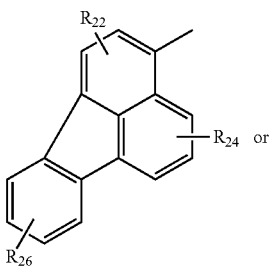

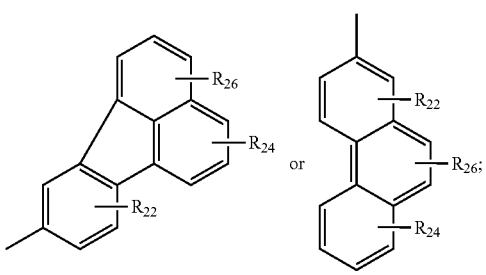

$E_2'$ is independently as defined for $E_1'$ or corresponds to the formula

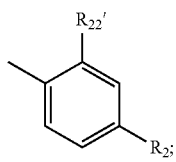

and the other groups are as defined above.
Preferably, $E_1$ is not

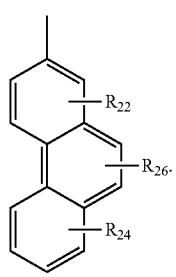

Even more preferred is a compound, wherein
$E_1'$ is the formula

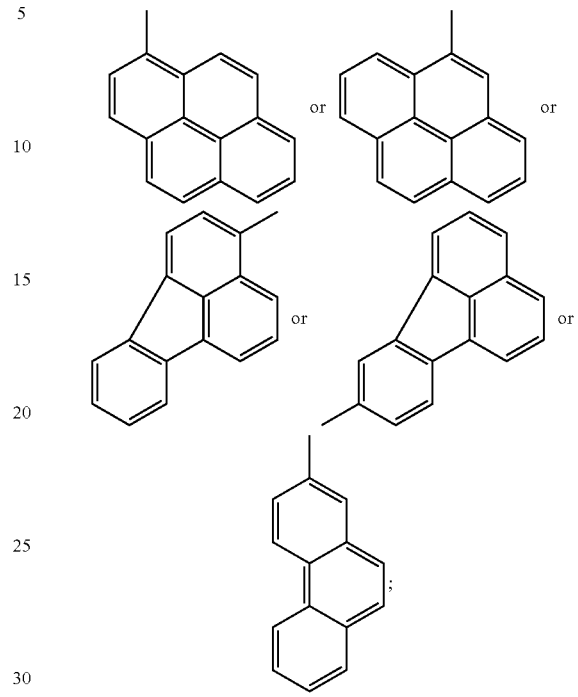

$E_2$ is independently as defined for $E_1'$ or corresponds to the formula

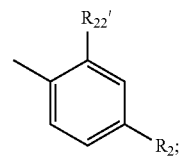

$R_1$ is H, $C_1$-$C_{12}$alkyl or $OR_3$;
$R_2$ is H, $C_1$-$C_8$alkyl; or $OR_3$;
$R_3$ is independently H, $C_1$-$C_{18}$alkyl; or $C_1$-$C_{12}$alkyl that is substituted by OH, $C_1$-$C_{18}$alkoxy, $COOR_4$ and/or by —O—CO—$R_5$;
$R_4$ is independently $C_1$-$C_{18}$alkyl;
$R_5$ is independently H; $C_1$-$C_{18}$alkyl; or $C_7$-$C_{11}$phenylalkyl;
$R_{11}$ is H; and
$R_{22}'$ is H, methyl or $OR_3$.

Most preferred is a compound, wherein
$E_1'$ is the formula

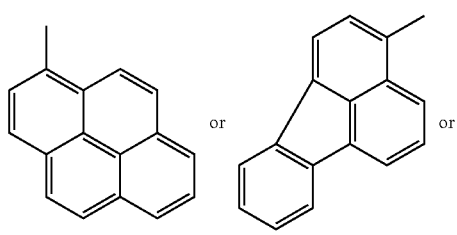

-continued

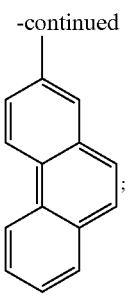

$E_2'$ is independently as defined for $E_1'$ or corresponds to the formula

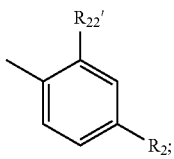

$R_1$ and $R_2$ are independently $OR_3$;
$R_3$ is independently H, $C_1$-$C_{18}$alkyl; or $C_1$-$C_{12}$alkyl that is substituted by OH, $C_1$-$C_{18}$alkoxy and/or $COOR_4$;
$R_4$ is independently $C_1$-$C_{18}$alkyl;
$R_{11}$ is H; and
$R_{22}'$ is $OR_3$, preferably OH.

Preferably, $E_1$ is not

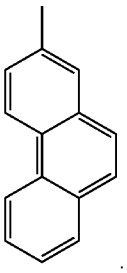

For example, $R_3$ is independently H, $C_1$-$C_{18}$alkyl; or $C_1$-$C_{12}$alkyl that is substituted by OH and/or $C_1$-$C_{18}$alkoxy. For instance, $R_3$ is not $C_1$-$C_{18}$alkyl.

For instance, $R_{11}$ is as defined above in this description.

For example, $R_{22}'$ is OH.

The triazines of the present invention are generally useful as UV-absorbers in various substrates. So another aspect of this invention is a composition stabilized against light-induced degradation which comprises, (a) an organic material subject to light-induced degradation, and
(b) a compound of formula (I).

For example, the composition comprises further additives. Examples of further additives are subsequently given.

1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutyl phenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methyl phenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidenebisphenols, for example 2, 2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2, 6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3, 5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethyl benzene, 1,4-bis(3,5-di-tert-butyl-4-hydroxybenzyl)-2,3,5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard® XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

2. UV absorbers and light stabilizers 2.1. Benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)

benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-(α,α-dimethyl benzyl)-5'-(1,1,3,3-tetramethylbutyl)-phenyl]-benzotriazole; 2-[2'-hydroxy-3'-(1,1,3,3-tetra methyl butyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-tri hydroxy and 2'-hydroxy-4,4'-dimethoxy derivatives.

2.3. Benzoates, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, such as α-cyanoacrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as nbutylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxy-pyrazole, with or without additional ligands.

2.6. Sterically hindered amine stabilizers, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino) ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydrooxy-2-methylpropoxy)-4-octadecanoyloxy-2,2,6,6-tetramethylpiperidine, 5-(2-ethyl hexanoyl)oxymethyl-3,3,5-trimethyl-2-morpholinone, Sanduvor® (Clariant; CAS Reg. No. 106917-31-1], 5-(2-ethylhexanoyl)oxymethyl-3,3,5-trimethyl-2-morpholinone, the reaction product of 2,4-bis [(1-cyclohexyloxy-2,2,6,6-piperidine-4-yl)butylamino]-6-chloro-s-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxanilides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. s-Triazines, for example 2, 4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis (4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy) phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydrooxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyldihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumyl phenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butyl phenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethyl hexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:
Tris(2,4-di-tert-butylphenyl)phosphite (Irgafos ®168, Ciba Specialty Chemicals Inc.), tris(nonylphenyl)phosphite, (A)
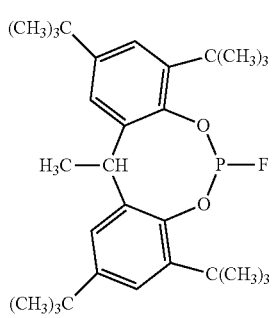

(B)
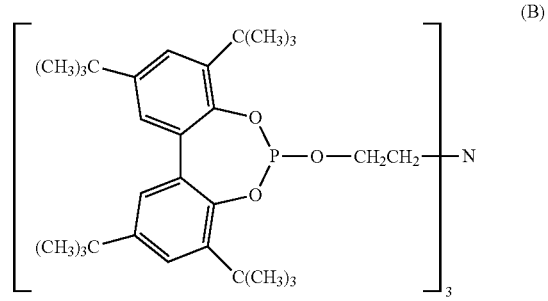

(C)
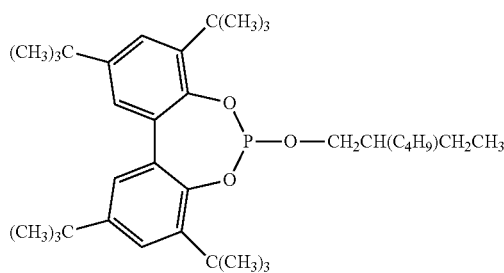

(D)
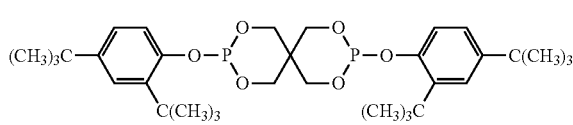

(E)
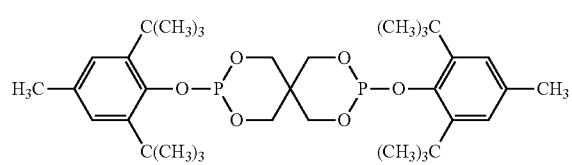

(F)
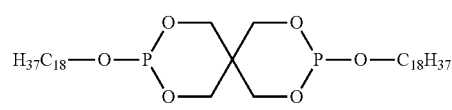

(G)
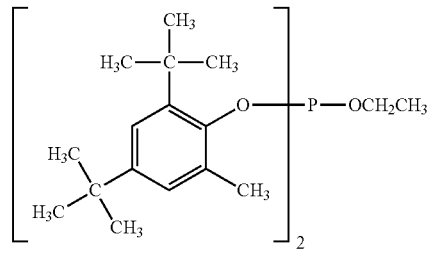

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octylalpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alphahexadecylnitrone, nitrone derived from N,N-dialkylhydroxylamine derived from hydrogenated tallow amine.

7. Thiosynemists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, Wallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethyl phenyl)-5,7-di-tert-butyl benzofuran-2-one, 3-(3,5-dimethyl-4-pivaloyloxyphenyl)-5,7-di-tert-butylbenzofuran-2-one, 3-(3,4-dimethyl phenyl)-5,7-di-tert-butyl benzofuran-2-one, 3-(2,3-dimethyl phenyl)-5,7-di-tert-butyl benzofuran-2-one, 3-(2-acetyl-5-isooctyl phenyl)-5-isooctylbenzofuran-2-one.

For instance, the further additives are phenolic and/or aminic antioxidants, sterically hindered amine stabilizers, UV-absorbers different from those of formula (I), phosphites, phosphonites, benzofuranones, metal stearates, metal oxides, pigments, dyes, organophosphorus compounds, hydroxylamines and/or flame retardants.

Preferably, such further additives are sterically hindered amine stabilizers and/or UV absorbers selected from the group consisting of the oxanilides, the hydroxybenzophenones, the benzoates, the α-cyanoacrylates, the benzotriazoles and the s-triazines different from those of formula (I).

When additional UV-absorbers are added they are preferably added in an amount from 0.1% to 30%, more preferably from 0.5% to 15% and most preferably from 1% to 10% by weight, based on the weight of the organic material. For instance, these preferences apply for coatings, coating compositions and recording material. For example, in polymer compositions, the additional UV-absorbers are added in amounts from 0.1% to 10%, preferably from 0.1 to 5%, especially 0.1 to 2%, based on the weight of the organic material.

When a sterically hindered amine stabilizer is additionally added, it is preferably added in an amount from 0.1% to 10%, more preferably from 0.5% to 5% and most preferably from 1% to 3% by weight, based on the weight of the organic material. For example, these preferences apply for coatings, coating compositions and recording material. For instance in polymer compositions, the amount of the sterically hindered amine stabilizer is from 0.1 to 5%, preferably from 0.1 to 2%, in particular from 0.1 to 0.5% based on the weight of the organic material.

The total amount of UV-absorber of formula (I) and other UV-absorbers and/or sterically hindered amine stabilizer is for example from 0.5% to 15% by weight, based on the weight of the organic material.

Examples for the sterically hindered amine stabilizers and UV-absorbers of the different classes are given above.

Particularly preferred UV-absorbers are the following s-triazines and benzotriazoles:

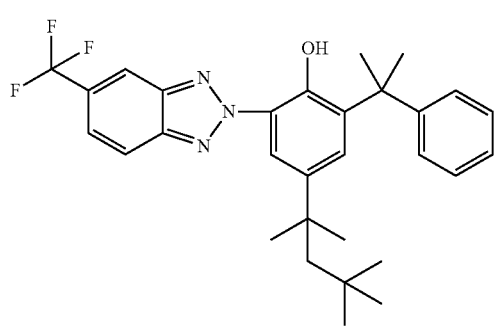
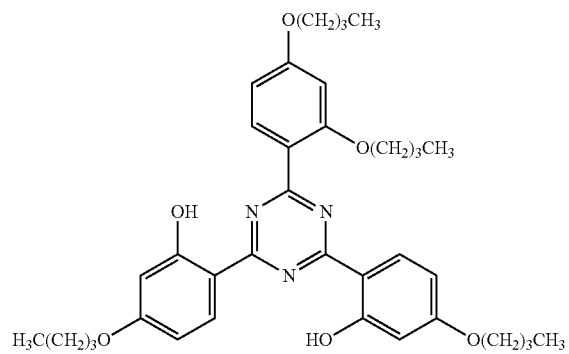

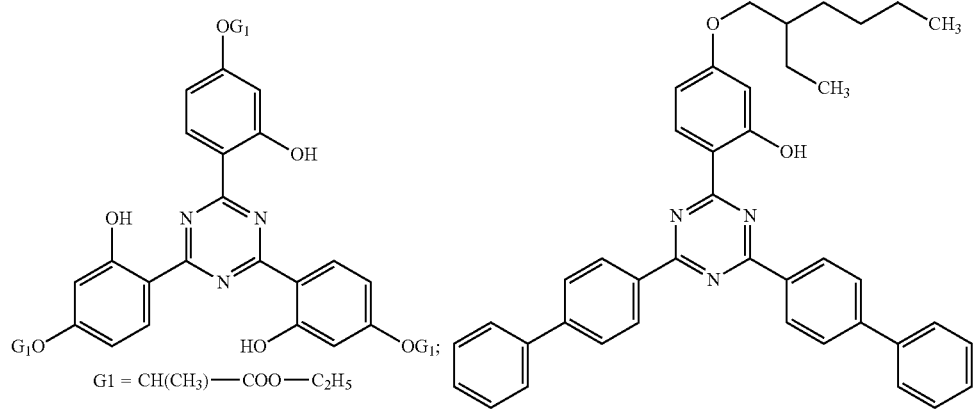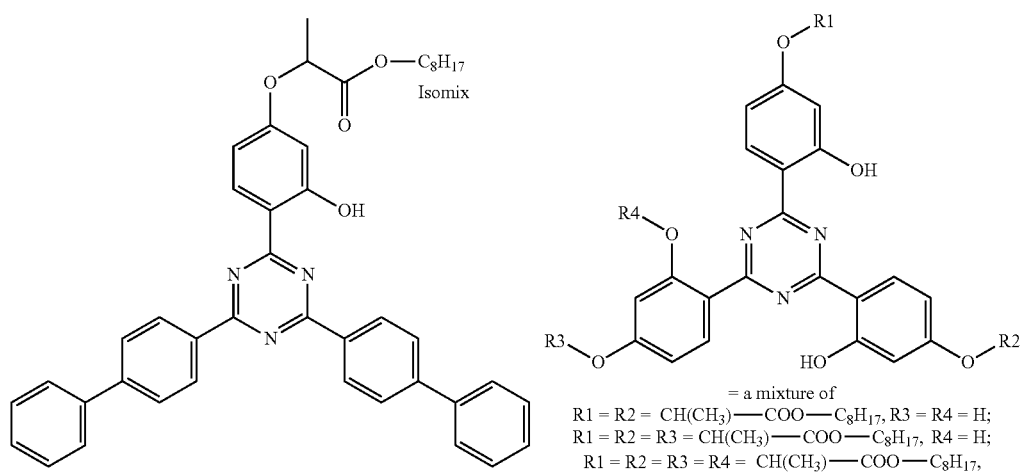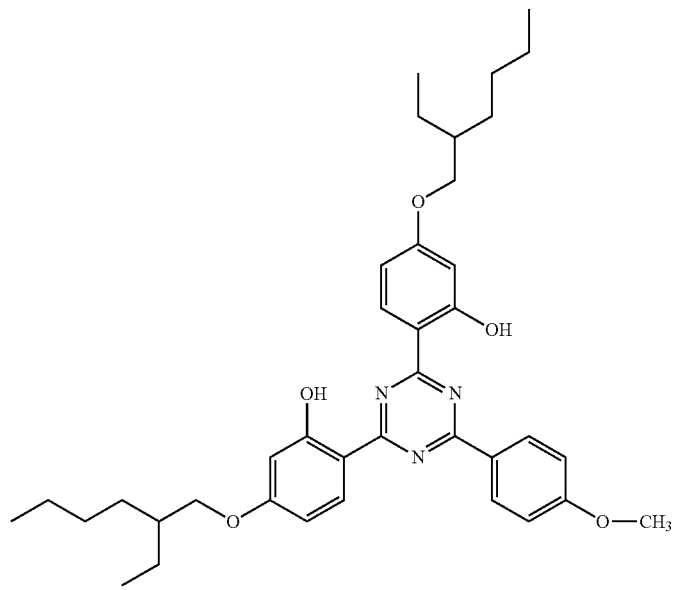

-continued
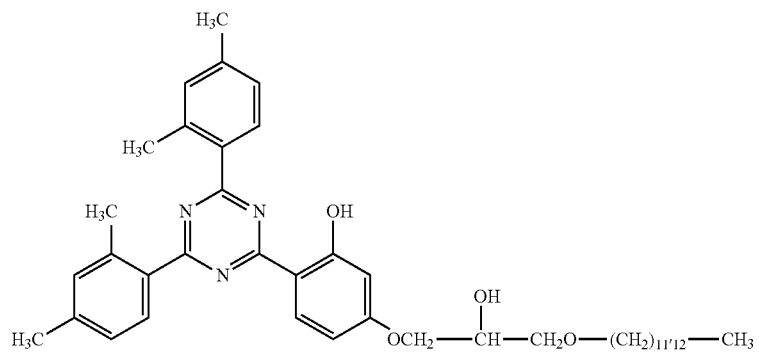
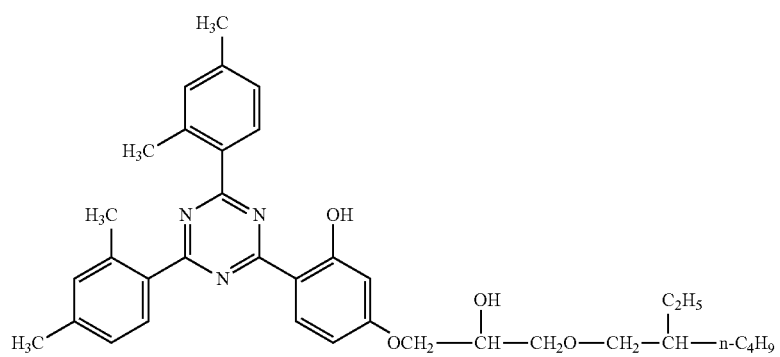
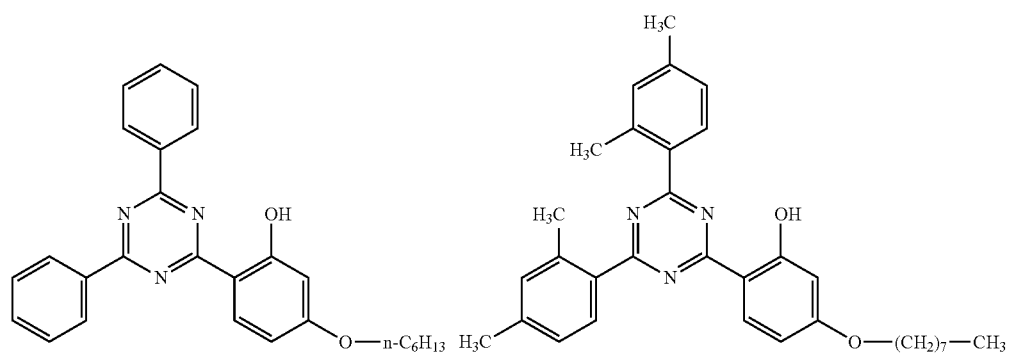
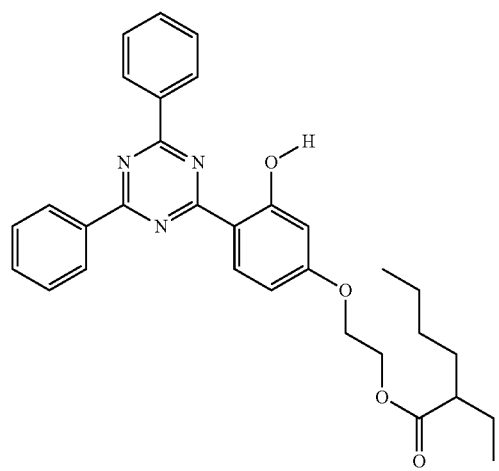

The hydroxyphenyl triazine UV-absorbers are known and are partially items of commerce.

The most suitable benzotriazole UV-absorbers are commercially available under the Trade Names TINUVIN® 384, TINUVIN® 928, TINUVIN® 900, TINUVIN® 328 and TINUVIN® 1130.

Preferred oxanilide UV-absorbers include SANDUVOR® VSU and SANDUVOR® 3206.

Preferred hydroxybenzophenones include CHIMASSORB® 81 and UVINUL® 3049.

The sterically hindered amine stabilizers are preferably selected from the group consisting of the following commercial products:

DASTIB® 845, TINUVIN® 770, TINUVIN® 765, TINUVIN® 144, TINUVIN® 123, TINUVIN® 111, TINUVIN® 783, TINUVIN® 791, TINUVIN® 123, TINUVIN® 292, TINUVIN® 152, TINUVIN® 144, MARK® LA 52, MARK® LA 57, MARK® LA 62, MARK® LA 67, HOSTAVIN® N 20, HOSTAVIN® N 24, SANDUVOR® 3050, SANDUVOR® 3058, DIACETAM® 5, SUMISORB® TM 61, UVINUL® 4049, SANDUVOR® PR 31, GOODRITE® UV 3034, GOODRITE® UV 3150, GOODRITE® UV 3159, GOODRITE® 3110×128, UVINUL® 4050 H, CHIMASSORB® 944, CHIMASSORB® 2020, CYASORB® UV 3346, CYASORB® UV 3529, DASTIB® 1082, CHIMASSORB® 119, UVASIL® 299, UVASIL® 125, UVASIL® 2000, UVINUL® 5050 H, LICHTSCHUTZSTOFF® UV 31, LUCHEM® HA B 18, MARK® LA 63, MARK® LA 68, UVASORB® HA 88, TINUVIN® 622, HOSTAVIN® N 30 and FERRO® AM 806.

Particularly preferred are TINUVIN® 770, TINUVIN® 292, TINUVIN® 123, TINUVIN® 144, TINUVIN® 152 and SANDUVOR® 3058.

Of interest is the organic material which is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example paper or plastic film, which has been coated with one or more layers. Depending on the type of the material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448.

The recording material can also be transparent, as, for example, in the case of projection films.

The compounds of the formula (I) can be incorporated into the carder material as early as the production of the latter, in the production of paper, for example, by being added to the paper pulp. A second method of application is to spray the carder material with an aqueous solution of compounds of the formula (I) or to add the compounds to the coating composition.

Coating compositions intended for transparent recording materials suitable for projection cannot contain any particles which scatter light, such as pigments and fillers.

The dye-binding coating composition can contain a number of other additives, for example antioxidants, light stabilizers (including also UV absorbers which do not belong to the UV absorbers according to the invention), viscosity improvers, fluorescent brighteners, biocides and/or antistatic agents.

The coating composition is usually prepared as follows: the water-soluble components, for example the binder, are dissolved in water and stirred together. The solid components, for example fillers and other additives already described, are dispersed in this aqueous medium. Dispersion is advantageously carded out by means of devices, for example ultrasonic samples, turbine stirrers, homogenizers, colloid mills, bead mills, sand mills, high-speed stirrers and the like. The compounds of the formula (I) can be incorporated easily into the coating composition.

The recording material according to this invention preferably contains 1 to 5000 mg/m$^2$, in particular 50-1200 mg/m$^2$, of a compound of the formula (I).

As already mentioned, the recording materials according to the invention embrace a wide field. The compounds of the formula (I) can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,5365,463; 4,551,407; 4,562,137 and 4,608,330, also in EP-A 139,479; EP-A 162,664; EP-A 164,931; EP-A 237,024; EP-A 237,025 or EP-A 260,129. In all these systems, the compounds can be put into the dye-receiving layer. The compounds can, however, also be put into the donor layer in order to protect the colour formers from light.

Photographic materials which can be stabilized are photographic dyes and layers containing such dyes or precursors thereof, for example photographic paper and films. Suitable materials are, for example, described in U.S. Pat. No. 5,364,749. The compounds of the formula (I) act here as a UV filter against electrostatic flashes. In colour photographic materials couplers and dyes are also protected against photochemical decomposition.

The instant compounds can be used for all types of colour photographic materials. For example, they can be employed for colour paper, colour reversal paper, direct-positive colour material, colour negative film, colour positive film, colour reversal film, etc. They are preferably used, inter alia, for photographic colour material which contains a reversal substrate or forms positives.

Colour-photographic recording materials usually contain, on a support, a blue-senitive and/or a green-sensitive and/or a red-sensitive silver-halide emulsion layer and, if desired, a protection layer, the compounds being, preferably, either in the green-sensitive or the red-sensitive layer or in a layer between the green-sensitive and the red-sensitive layer or in a layer on top of the silver-halide emulsion layers.

The compounds of the formula (I) can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, they can be employed in recording materials for dye diffusion transfer printing, thermal wax transfer printing and dot matrix printing and for use with electrostatic, electrographic, electrophoretic, magnetographic and laser-electrophotographic printers and pen-plotters. Of the above, recording materials for dye diffusion transfer printing are preferred as, for example described in EP-A-507,734.

They can also be employed in inks, preferably for ink jet printing, as, for example, further described in U.S. Pat. No. 5,098,477.

Of further interest is the organic material which is a natural, semi-synthetic or synthetic polymer, especially a thermoplastic polymer.

Examples of such polymers are given below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methyl pentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethyllene-propylene copolymers, LDPE/ethylene-vinyl acetate copolymers (EVA), LDPE/ethyleneacrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethyllene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or polym-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Of interest is the use of the instant compounds as stabilizers in synthetic organic polymers, for example a coating or a bulk polymer or article formed therefrom, especially in thermoplastic polymers and corresponding compositions as well as in coating compositions, for example in acid or metal catalyzed coating compositions.

In general the instant compounds are added to the organic polymer to be stabilized in amounts of from 0.01 to 10%, preferably from 0.01 to 5%, in particular from 0.01 to 2% (based on the organic polymer to be stabilized). Particular preference is given to the use of the instant compounds in amounts of from 0.05 to 1.5%, especially from 0.1 to 0.5%.

Incorporation into the organic polymers can be effected, for example, by mixing in or applying the instant compounds and, if desired, further additives by the methods which are customary in the art. The incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the instant compounds into polymers is to add them before, during or directly after the polymerization of the corresponding monomers or prior to crosslinking. In this context the instant compounds can be added as it is or else in encapsulated form (for example in waxes, oils or polymers).

The instant compounds can also be added in the form of a masterbatch containing said compound in a concentration, for example, of from 2.5 to 25% by weight to the polymers that are to be stabilized.

The instant compounds can judiciously be incorporated by the following methods:
- as emulsion or dispersion (e.g. to latices or emulsion polymers),
- as a dry mixture during the mixing in of additional components or polymer mixtures,
- by direct introduction into the processing apparatus (e.g. extruders, internal mixers, etc),
- as solution or melt.

Novel polymer compositions can be employed in various forms and/or processed to give various products, for example as (to give) films, fibres, tapes, moulding compositions, profiles, or as binders for coating materials, adhesives or putties.

For example, the organic material is a coating composition, especially an automotive coating composition.

For instance, the organic material is a coating, in particular an automotive coating.

Resins used in coatings are typically crosslinked polymers, for example, derived from aldehydes on the one hand and phenols, ureas and melamines on the other hand, such as phenol/formaldehyde resins, urea/formaldehyde resins and melamine/formaldehyde resins.

Also useful are unsaturated polyester resins derived from copolyesters of saturated and unsaturated dicarboxylic acids with polyhydric alcohols and vinyl compounds as crosslinking agents, and also halogen-containing modifications thereof of low flammability.

Preferably used are crosslinkable acrylic resins derived from substituted acrylates, for example epoxy acrylates, urethane acrylates or polyester acrylates.

Also possible are alkyd resins, polyester resins and acrylate resins crosslinked with melamine resins, urea resins, isocyanates, isocyanurates, polyisocyanates or epoxy resins.

Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

The coating material may also be a radiation curable composition containing ethylenically unsaturated monomers or oligomers and a polyunsaturated aliphatic oligomer.

The alkyd resin lacquers which can be stabilized against the action of light in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99-123). Other crosslinking agents include glycouril resins, blocked isocyanates or epoxy resins.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When water-soluble, water miscible or water dispersible coatings are desired, ammonium salts of acid groups present in the resin are formed. Powder coating composition can be prepared by reacting glycidyl methacrylate with selected alcohol components.

Most preferably, the organic material is an automotive coating comprising the following layers
d) a cathodically deposited coating, adhering to a metal substrate;
e) at least one subsequent coating layer containing a compound of formula (I) adhering to the cathodically deposited coating; and
f) a clear top coating containing one or more UV-absorbers different from those of formula (I) and optionally further lightstabilizers.

For instance, the coating layer e) is directly next to the coating layer d) and the coating layer f) is directly next to the coating layer e).

For example, in such an automotive coating, the metal substrate is pretreated in e.g. a customatry zinc phosphate bath.

Of interest is the composition wherein the coating is applied onto a substrate, which is sensitive to electromagnetic radiation of wavelengths greater than 380 nm.

A typical sensitive substrate is, for example, a cathodically deposited coating adhering to a metal substrate. Such coatings are typically used in the automotive industry.

Under sensitive to electromagnetic radiation of wavelengths greater than 380 nm there is understood UV or visible light, for example, in the wavelength range up to 450 nm, preferably up to 440 nm and in particular up to 420 nm.

For instance, in the instant composition the compound of formula (I) is present in an amount of from 0.1% to 30% by weight, preferably from 0.5% to 15% and more preferably from 1% to 10% by weight, based on the weight of the organic material. These concentrations are of particular interest for coating compositions or coatings or recording material. The preferred concentrations for polymer compositions are given above.

A further aspect of the instant invention is a process for the stabilization of an organic material against the deleterious influence of UV and/or visible light, which comprises admixing and/or applying to said material as stabilizer a compound of formula (I).

For instance, in this process the organic material is a coating, especially an automotive coating.

In particular, in this process the organic material is an automotive coating, comprising
g) applying a cathodically deposited coating, adhering to a metal substrate;

h) incorporating into at least one coating adhering to the cathodically deposited coating a compound of formula (I); and j) applying a clear top coating over the coating adhering to the cathodically deposited coating, which clear top coating contains one or more UV-absorbers different from those of formula (I) and optionally further lightstabilizers.

For instance, the coating layer h) is directly next to the coating layer g) and the coating layer j) is directly next to the coating layer h).

Another aspect of the invention is the use of a compound of formula (I) as ultraviolet (UV) and visible (VIS) light absorber in organic material which is subject to light-induced degradation.

For instance, for this use the organic material is a coating, in particular an automotive coating.

The definitions and preferences given for the compounds apply also for the other aspects of the invention.

Percentages given are weight percentages unless otherwise stated.

The following examples illustrate the invention.

EXAMPLES

All reactions are performed under inert and dry conditions unless otherwise stated.

Abbreviations:
$^1$H-NMR: Bruker 300/400 MHz (CDCl$_3$, DMSO-d$^6$)
RT: room temperature
mp: melting point (° C.)
ε: extinction coefficient in l·mol$^{-1}$·cm$^{-1}$
$\lambda_{max}$: absorption maximum in nm
Commercial stabilizers used in the application examples:

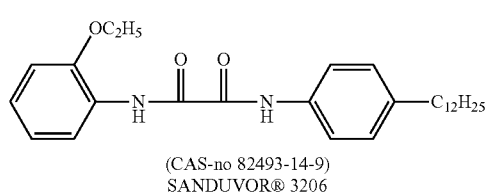

(CAS-no 82493-14-9)
SANDUVOR® 3206

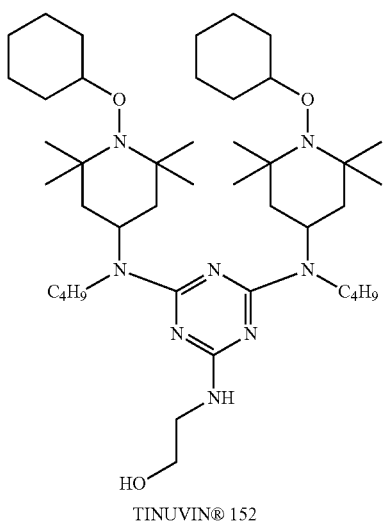

TINUVIN® 152

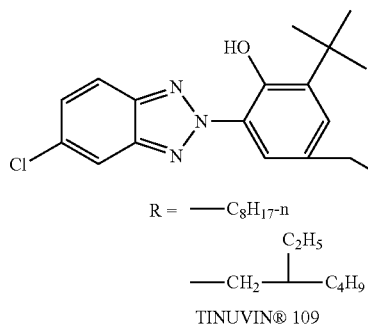

TINUVIN® 109

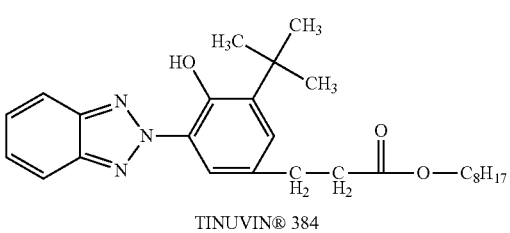

TINUVIN® 384

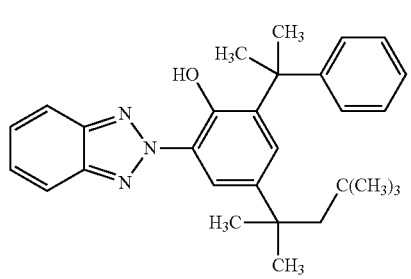

TINUVIN® 928

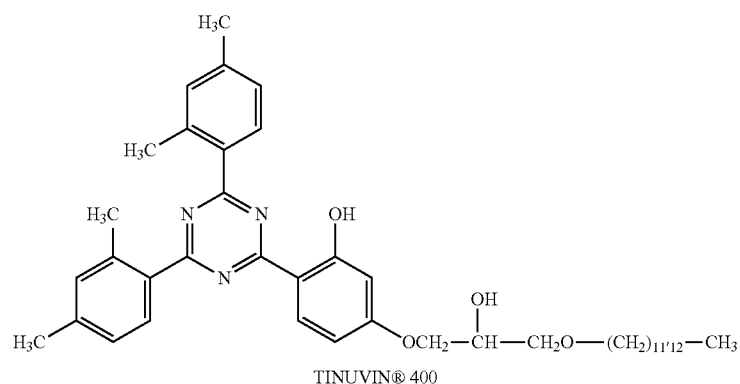

TINUVIN® 400

Example 1

Preparation of Starting Material

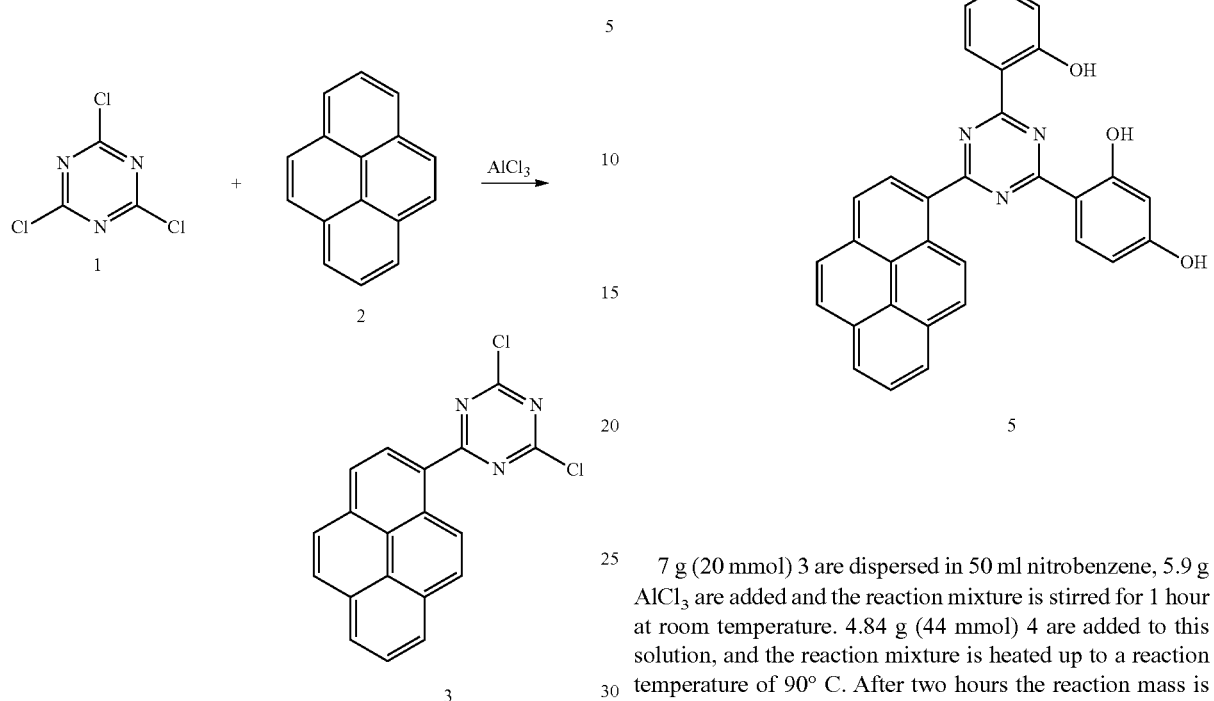

18.5 g (0.1 mol) 1 and 20.5 g (0.1 mol) 2 are dissolved in 350 ml chlorobenzene. The solution is cooled to a temperature of 0-5° C. and within 15 minutes 14.7 g AlCl₃ are added in portions to this solution. A suspension is formed, which is stirred for two hours at a reaction temperature of below 5°. The reaction is worked up by adding 200 ml of cold methanol to the reaction mixture. The product 3 is precipitated as crystals. The isolated crystals are dispersed in 200 ml 2N HCL for another one hour at T=0-5° C. The crystals of product 3 are filtered off and washed with water (yield: 84%).

M.p.3: 245-247° C.

Example 2

7 g (20 mmol) 3 are dispersed in 50 ml nitrobenzene, 5.9 g AlCl₃ are added and the reaction mixture is stirred for 1 hour at room temperature. 4.84 g (44 mmol) 4 are added to this solution, and the reaction mixture is heated up to a reaction temperature of 90° C. After two hours the reaction mass is cooled down to room temperature and the mass is quenched by addition of 200 ml 2N HCL. Product 5 is precipitated as crystals and filtered off. The crystals are washed in 200 ml methanol, separated by filtration and dried at 70° C. Product 5 is isolated in 85% yield. M.p.5:>310° C.

Example 3

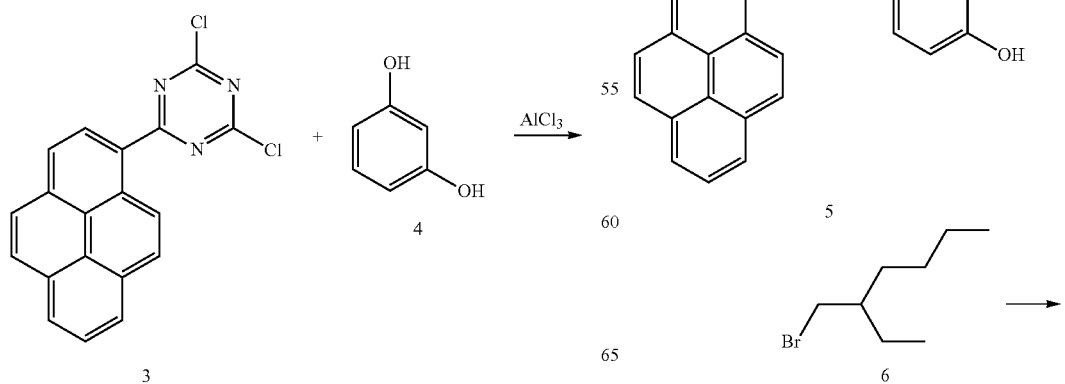

-continued

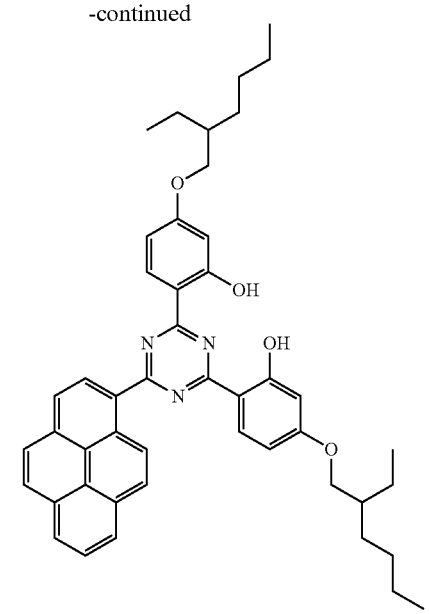

7

8 g (16.1 mmol) 5 and 4.9 g potassium carbonate are dissolved in 50 ml dimethyl-formamide. The solution is heated up to T=100° C. and then 6.83 g (35 mmol) 6 are added. The reaction mixture is kept for three hours at this temperature and then cooled down to room temperature and hydrolyzed by addition of 20 ml water. Product 7 is precipitated as crystals and purified by column chromatography (silica gel, toluene as eluant). After purification product 7 is isolated as fraction in 40% yield. M.p.7: 190-200° C.; UV/Vis (CHCl$_3$): $\lambda_{max}(\epsilon)$: 298.5 (41311), 361.5 (55791), 400 (25461), 436 (1972).

Example 4

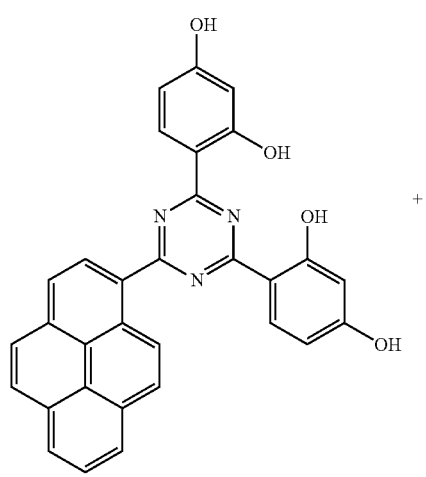

5

+

-continued

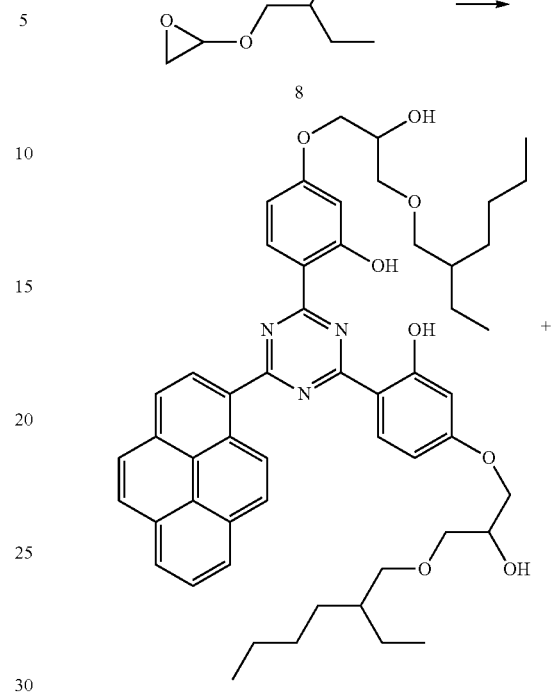

8

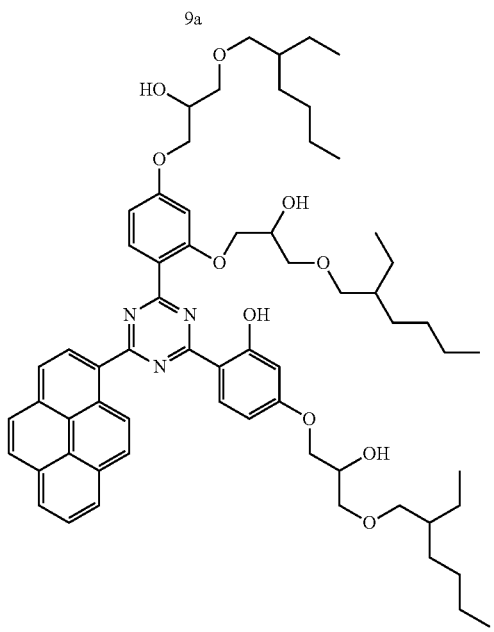

5 (10 mmol) 5 and 50 mg triphenyl-phosphoniumbromide are dissolved in 20 ml dimethylformamide. The reaction mixture is heated up to a reaction temperature of T=100° C. 3.7 g (20 mmol) 8 is added in portions and the reaction mixture is kept at T=105° C. until all epoxide 8 is reacted. The reaction mixture is cooled down to room temperature diluted with CH$_2$Cl$_2$ and the organic phase is washed with water. The organic phase is dried over MgSO$_4$, and the solvent is distilled off. The product mixture consists of Product 9a (76%) and the product 9b (15%). Product 9a is purified by column chromatography (silica gel, toluene as eluant) and obtained as fraction with a yield of 73%. M.p.9a: 170-175° C.; UV/Vis (CHCl$_3$): $\lambda_{max}(\epsilon)$: 299 (46400), 358.5 (53700), 400 (26000).

The product 9b is isolated as first fraction by the above column chromatography (R$_f$=0.18, toluene) with a yield of 12%. 9b: oil; UV/Vis (CHCl$_3$): $\lambda_{max}(\epsilon)$: 293 (41400), 345 (36700), 400 (22000).

Example 5

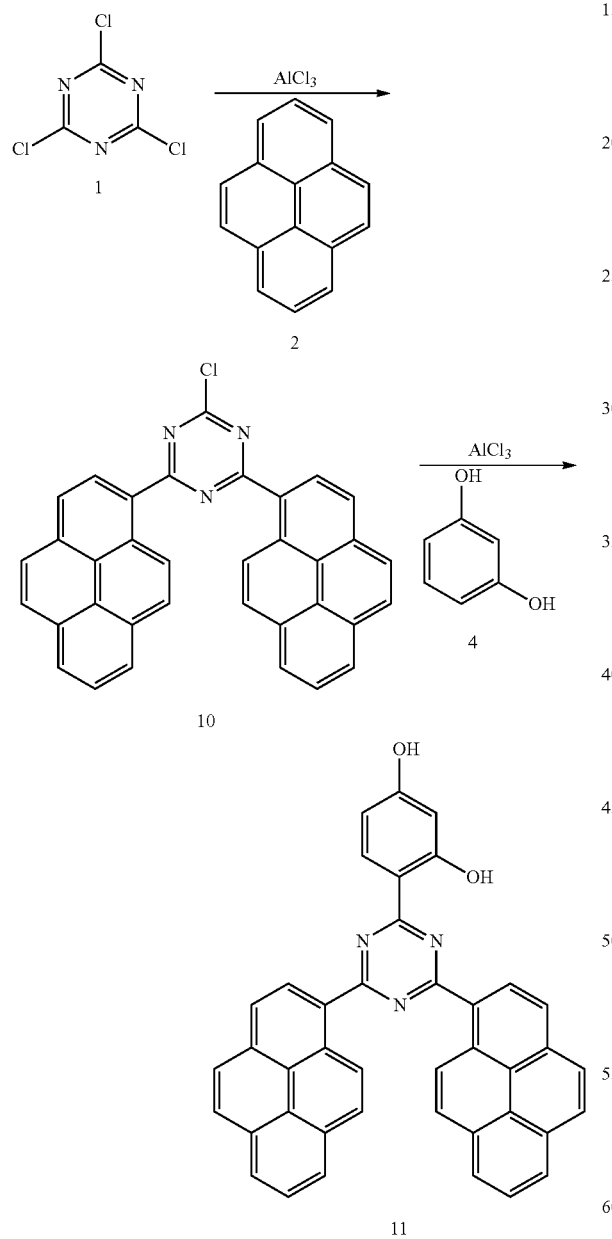

9.2 g (0.05 mol) 1 and 20.2 g (0.1 mol) 2 are dissolved in 250 ml chlorobenzene. The solution is cooled to a temperature of T=0-5° C. and within 15 minutes 14.7 g AlCl$_3$ are added in portions to this solution. A suspension is formed, which is stirred for two hours at a reaction temperature of below 5° C. The reaction mixture is heated up to T=50° C. until all pyrene 2 is reacted. The reaction mixture with intermediate 10 is cooled down to T=50° C. and another 11 g AlCl$_3$ are added and the reaction mixture is stirred for 30 minutes. Afterwards 11 g 4 are added and the reaction temperature is raised to T=105° C. After the reaction is completed, the reaction mass is cooled down to room temperature and the mass is quenched by addition of 200 ml 2N HCL. Product 11 is precipitated and filtered off. The crystals are washed in 200 ml methanol, separated by filtration and dried at 70° C. Product 11 is obtained in 66% yield. M.p.11:>300° C.

Example 6

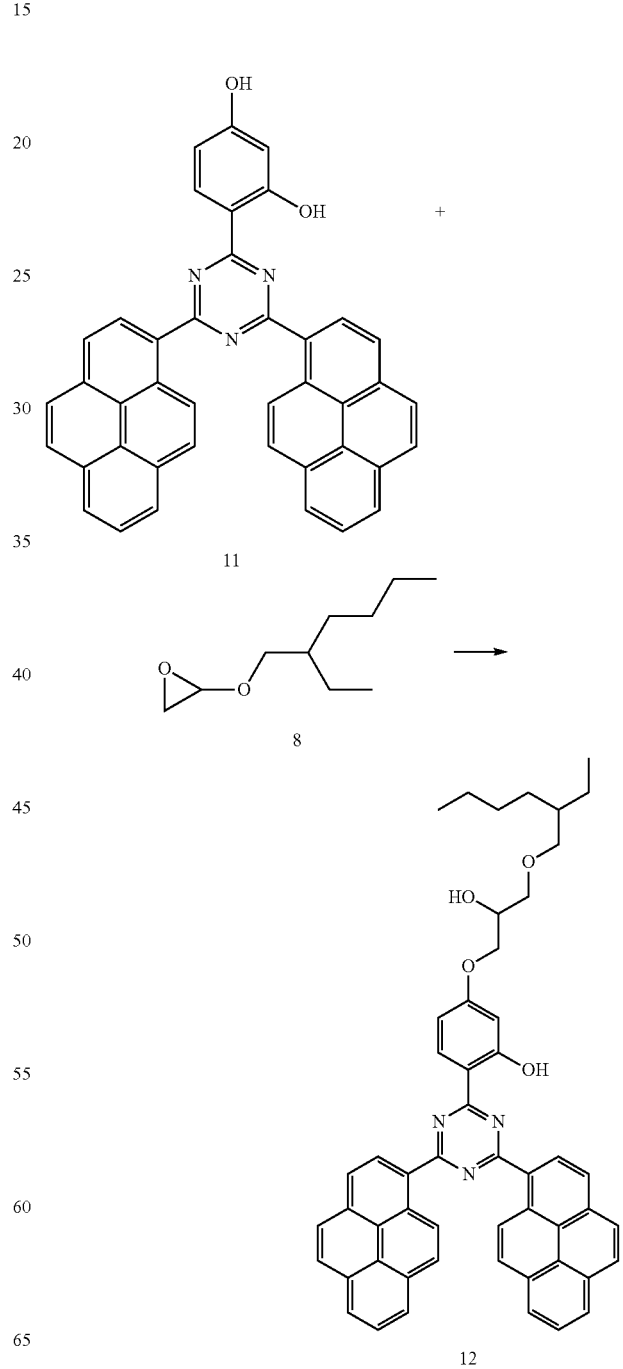

5 (8.5 mmol) 11 and 50 mg triphenyl-phosphoniumbromide are dissolved in 10 ml dimethylformamide. The reaction mixture is heated up to a reaction temperature of T=140° C. 3.05 g (16 mmol) 8 is added in portions and the reaction mixture is kept at T=140° C. until the reaction is finished. The reaction mixture is cooled down to room temperature and the product is precipitated in 200 ml methanol. The crude product is purified by column chromatography (silica gel, toluene as eluant). Product 12 is obtained as fraction in form of crystals with a yield of 54%. M.p.12: 245-250° C.; UV/Vis (CHCl$_3$): $\lambda_{max}(\epsilon)$: 295.5 (55700), 377 (54115), 400 (49500).

Example 7

Example 8

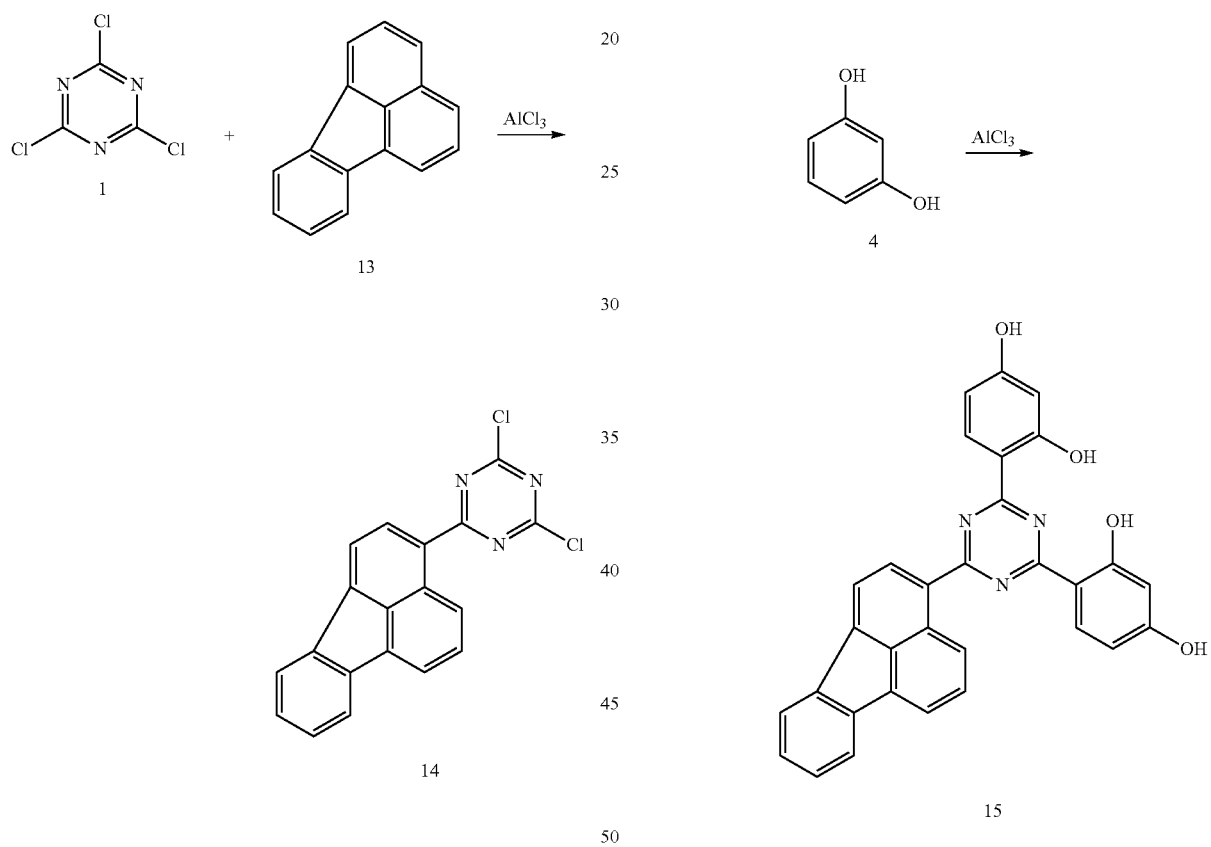

9.25 g (50 mmol) 1 and 10.1 g (50 mmol) 13 are dissolved in 100 ml benzene. The solution is cooled to a temperature of 0-5° C. and within 60 minutes 7.5 g AlCl$_3$ are added in portions to this solution. A solution is formed which is stirred for twenty hours while the reaction mixture is warmed up to room temperature. The suspension is precipitated in 200 ml cold methanol and product 14 is isolated as crystals. The isolated crystals are dispersed in 200 ml 2N HCL for another one hour at T=0-5° C. The crystals of product 14 are filtered off and washed with water and finally recrystallised from toluene. Product 14 is obtained in form of crystals with a yield of 85%. M.p.14: 230-240° C.

6 g (17 mmol) 14 are dissolved in 120 ml nitrobenzene, 5 g AlCl$_3$ are added and the reaction mixture is stirred for 1 hour at room temperature. 4.15 g (37 mmol) 4 are added to this solution, and the reaction mixture is heated up to a reaction temperature of 90° C. After eighteen hours the reaction mass is cooled down to room temperature and the mass is quenched by addition of 200 ml 2N HCL. Product 15 is precipitated as crystals and filtered off. The crystals are washed in 200 ml methanol, separated by filtration and dried at 70° C. Product 15 is recrystallised from hot di-methyl-formamide and obtained in 74% yield. M.p.15:>300° C.

Example 9

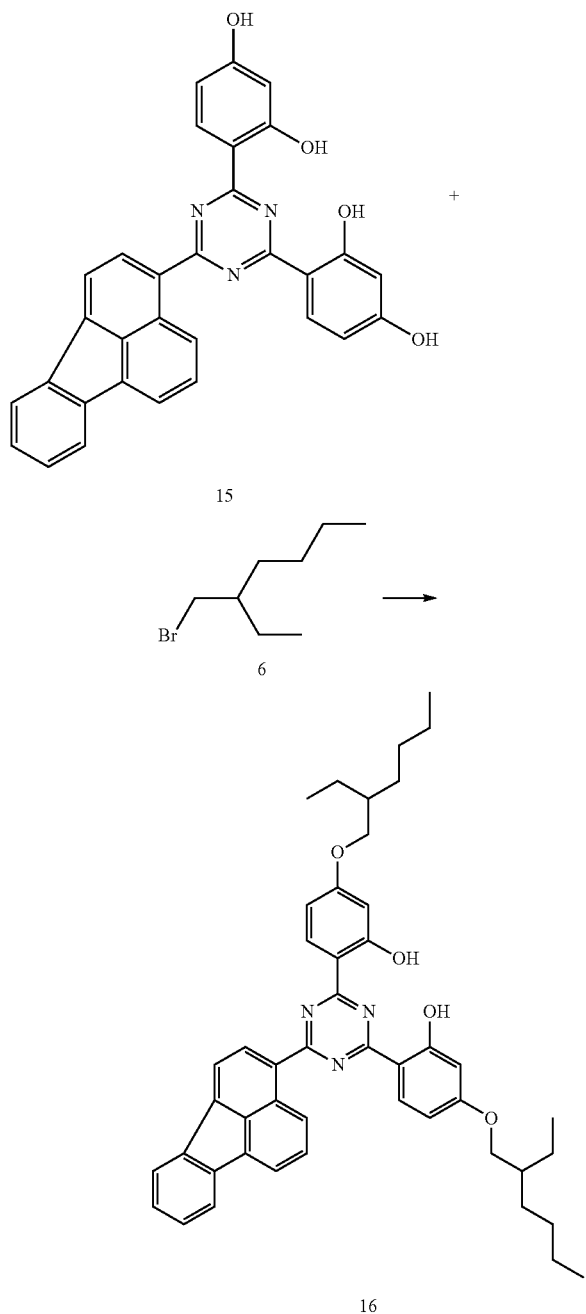

5 g (10 mmol) 15 and 3.04 g potassium carbonate are dissolved in 40 ml dimethyl formamide. The solution is heated up to a temperature of 100° C. and then 4.7 g (24 mmol) 6 are added. The reaction mixture is kept until all 6 is reacted and then cooled down to room temperature and hydrolyzed by addition of 20 ml water. The product is extracted by $CH_2Cl_2$. After distillation of the solvents, the crude product 16 is purified by column chromatography (silica gel, toluene, ethyl acetate as eluants) and obtained as fraction in 42% yield. M.p.16: 110-115° C.; UV/Vis ($CHCl_3$): $\lambda_{max}(\epsilon)$: 308.5 (37952), 364 (55348), 400 (16054), 436 (436).

Example 10

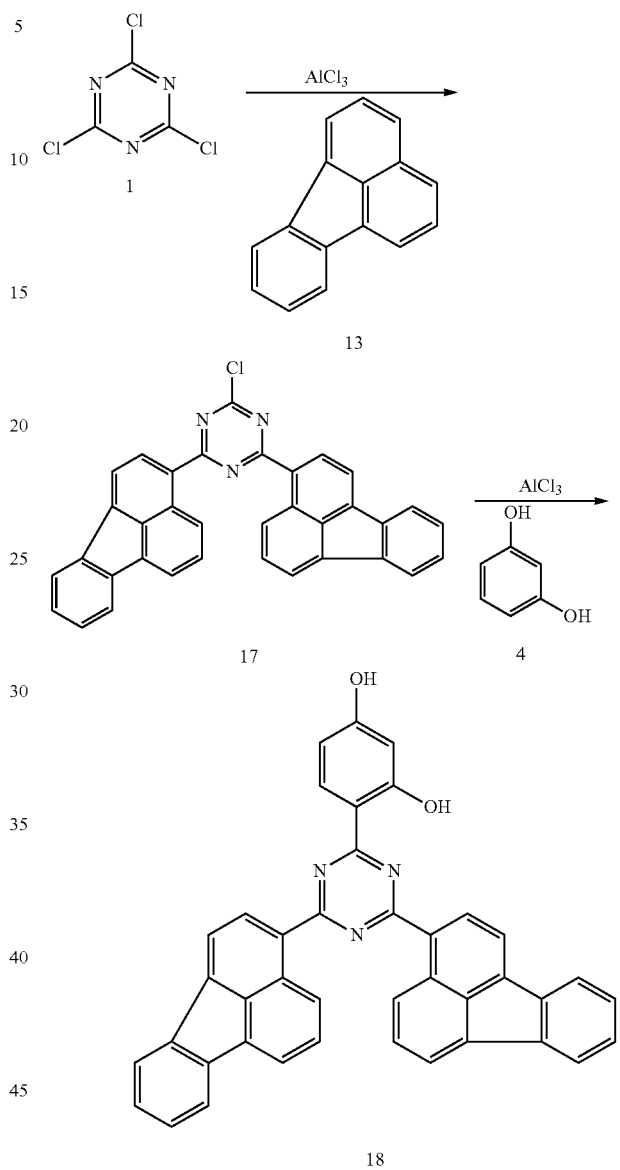

10 g (0.054 mol) 1 and 23.5 g (0.116 mol) 13 are dissolved in 300 ml chlorobenzene. The solution is cooled to a temperature of T=0-5° C. and within 30 minutes 14.8 g $AlCl_3$ are added in portions to this solution. A suspension is formed immediately, which is stirred for three hours at a reaction temperature of below 5°. The reaction mixture is then heated up to T=60° C. until all fluoranthene 13 is reacted. The reaction mixture containing intermediate 17 is cooled down to a temperature of T=60° C. Then 7.2 g $AlCl_3$ are added and the reaction mixture is stirred for 15 minutes. Then 8.9 g (8 mmol) 4 are added to this solution, and the reaction mixture is heated up to a reaction temperature of T=90° C. After the reaction is completed, the reaction mass is cooled down to room temperature and the mass is quenched by addition of 200 ml 2N HCL. Product 18 is precipitated and filtered off. The brownish colored crystals are washed in 200 ml methanol, separated by filtration and dried at 70° C. Product 18 is obtained in 41% yield. M.p.18: 280-285° C.

Example 11

Example 12

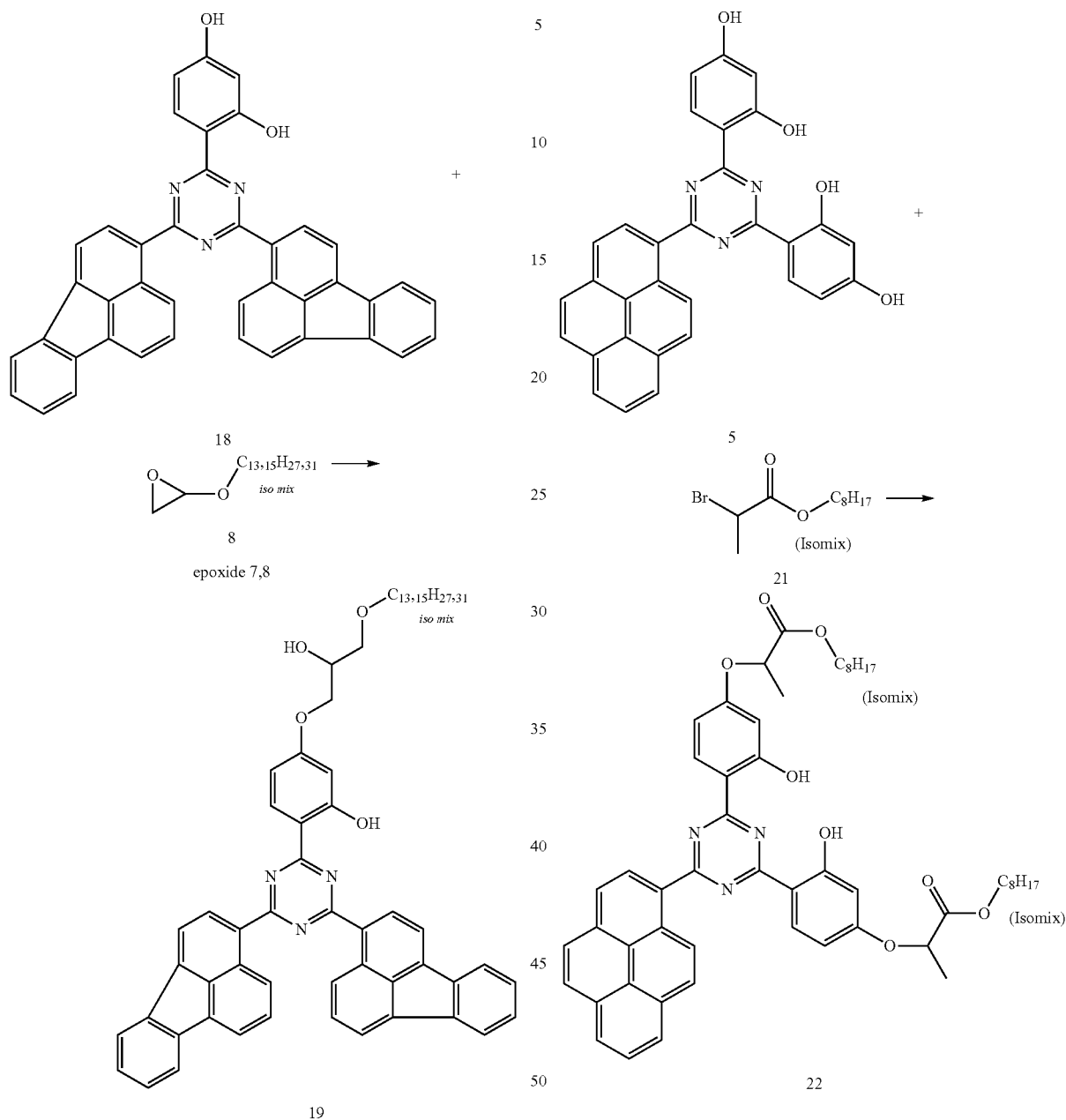

5 (8.5 mmol) 18 and 30 mg triphenyl-phosphoniumbromide are dissolved in 20 ml dimethylformamide. The reaction mixture is heated up to a reaction temperature of T=100° C. 7.2 g (25 mmol) epoxide 7,8 (isomer mixtures) 8 is added in portions and the reaction mixture is raised to a temperature of T=140° C. The reaction mixture is kept at this temperature for three hours. The reaction mixture is cooled down to room temperature diluted with toluene (hot) and the organic phase is washed with water. The organic phase is dried over MgSO$_4$, and the solvent is distilled off. The crude product 19 is purified by column chromatography (silica gel, toluene as eluant) and obtained as fraction in 34% yield. M.p.19:190-195° C.; UV/Vis (CHCl$_3$): $\lambda_{max}(\epsilon)$: 273 (43550), 307.5 (45823), 343.5 (37000), 375 (50360), 400 (35050).

5 g (10 mmol) 5 and 2.9 g potassium carbonate are dissolved in 7 ml dimethyl-formamide. The solution is heated up to T=100° C. and then 5.6 g (21 mmol) 21 diluted in 15 ml toluene are added to the reaction mixture. The reaction mixture is kept for three hours at this temperature and then cooled down to room temperature and hydrolyzed by addition of 20 ml water. The organic phase is separated and evaporated. The crude product 22 is purified by column chromatography (silica gel, toluene/ethyl acetate as eluant). After purification product 22 is isolated as fraction in 46% yield. M.p. 22: 146-152° C.; UV/Vis (CHCl$_3$): $\lambda_{max}(\epsilon)$: 298.5 (47521), 359 (50775), 365 (48007), 400 (25601), 436 (3421).

Example 13

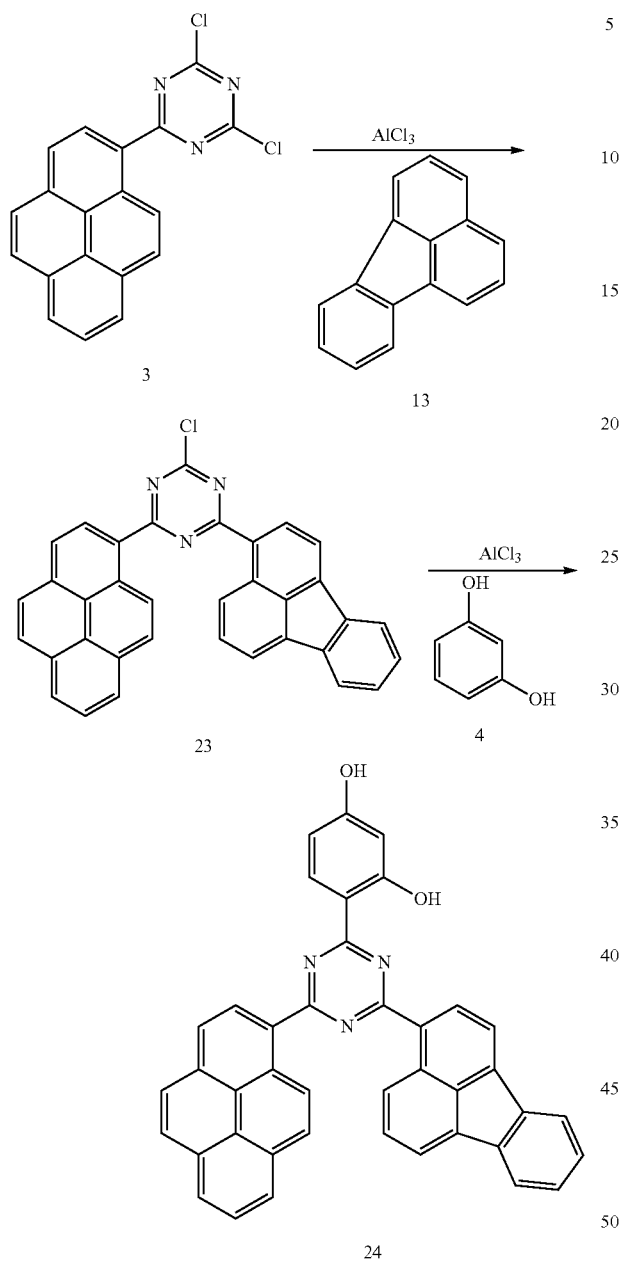

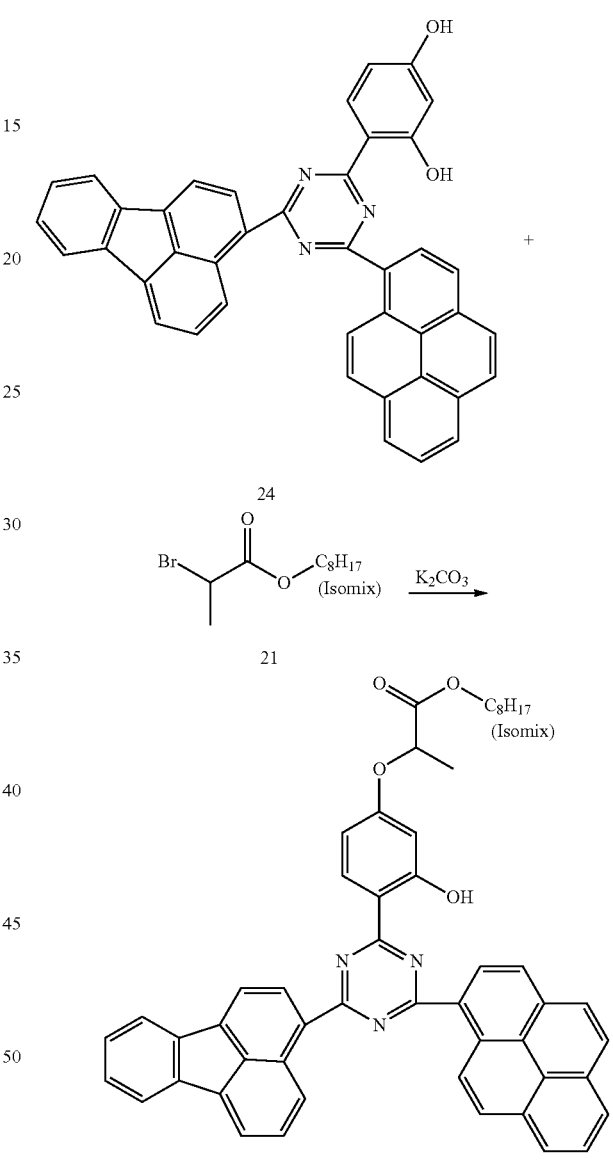

Compound 3 is prepared similarly to Example 1: 9.31 g (0.05 mol) 1 are dissolved in 100 ml dichlorobenzene. The solution is cooled down to a temperature of T=0-5° C. and within 30 minutes 20.2 g AlCl$_3$ (0.15 mol) are added in portions to this solution. A suspension is formed and 10 g (0.05 mol) 2 dissolved in 40 ml dichlorobenzene are added within 1 hour, a black suspension is formed, which is stirred for 2 hours at a reaction temperature of below 0°. 10 g (0.05 mol) 13 dissolved in 40 ml dichlorobenzene are added within 1 hour to the reaction mixture containing intermediate 3. The reaction mixture is then warmed up to T=25° C. and after 1 hour heated up to T=80° C. until all 3 is reacted. To the reaction mixture containing intermediate 23, 6.11 g (0.05 mol) 4 are added and the reaction mixture is heated up to T=120° C. After the reaction is completed, the reaction mass is cooled down to room temperature and the mass is quenched by addition of 200 ml 2N HCL. Product 24 is precipitated and filtered off. The crystals are washed in 200 ml methanol, separated by filtration and dried at 70° C. Product 24 is obtained in 3% yield. M.p.24: 308-311° C.

Example 14

0.5 g (0.8 mmol) 24 and 0.12 g potassium carbonate are dissolved in 2 ml dimethyl-formamide. The solution is heated up to T=100° C. and then 0.23 g (0.86 mmol) 21 diluted in 3 ml toluene are added to the reaction. The reaction mixture is kept for three hours at this temperature and then cooled down to room temperature and hydrolyzed by addition of 20 ml water. These two phases are separated and evaporated. The crude product 25 is purified by column chromatography (silica gel, toluene/ethyl acetate as eluant). After purification product 25 is isolated in 30% yield. M.p.25: 136-142° C.; UV/Vis (CHCl$_3$): $\lambda_{max}$: 298.5, 359, 365, 400, 436.

Example 15

Preparation of Starting Material

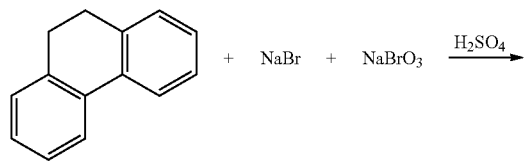

10 g (55 mmol) 26 is dissolved in 80 ml nitrobenzene, 20 g water is added. To this emulsion 3.9 g (38 mmol) sodium bromide and 2.4 g (16 mmol) sodium bromate are added. The reaction mixture is cooled down to T=0° C. and 11 g (25 mmol) sulfuric acid are added within 7 hours. Then the temperature is warmed up to room temperature and stirred for 3 hours. The product 27 is isolated by extraction with 100 ml dichloromethane and the organic phase is washed three times with 30 ml water. Product 27 is evaporated and purified by column chromatography (silica gel, heptane as eluant). Product 27 is isolated in 54% yield as oil.

Example 16

Preparation of Starting Material

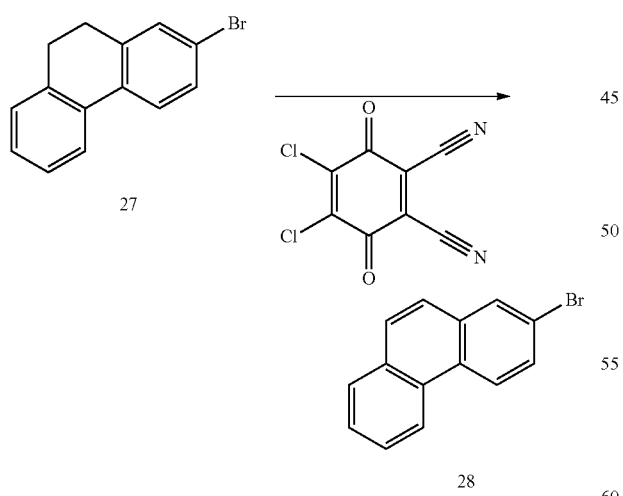

5.1 g (20 mmol) 27 is dissolved in 100 ml dioxane and 14.9 g (65 mmol) DDQ (4,5-dichloro-3,6-dioxo-1,4-cyclohexadiene-1,2-dicarbonitrile) is added. A black suspension is formed and the reaction mixture is heated up to T=100° C. and stirred for 24 hours. The reaction mixture is cooled down to room temperature and filtrated. Product 28 is isolated by evaporation and purified by column chromatography (silica gel, heptane as eluant). Product 28 is isolated in 67% yield as colorless crystals. M.p.28: 84-88° C.

Example 17

Preparation of Starting Material

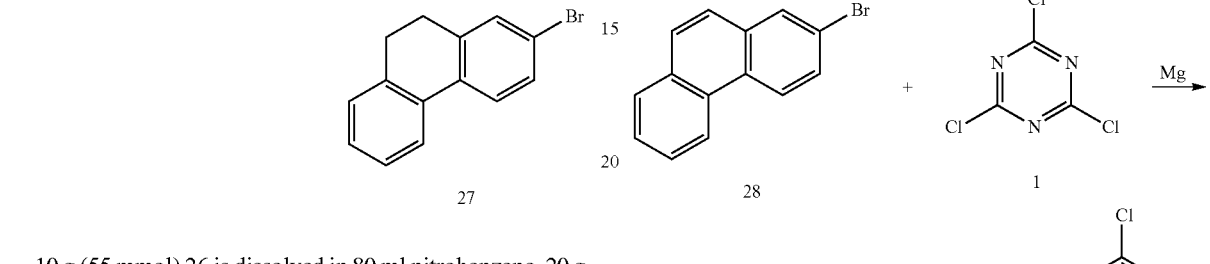

0.6 g (24 mmol) magnesium is suspended in 10 ml tetrahydrofuran. A solution of 2.1 g (8.2 mmol) 28 dissolved in 10 ml tetrahydrofuran is added within 30 min and the temperature is maintained for 2 hours at 80° C. This Grignard intermediate is then cooled to room temperature, filtered and added within 30 min to a cold (0° C.) suspension of 1.5 g (8.2 mmol) 1 in 10 ml tetrahydrofuran. A black suspension is formed and stirred for 24 hours. The reaction mixture is cooled down to room temperature and product 29 is isolated by filtration. The solid is kept on ice and extracted with dichloromethane; the organic phase is evaporated and dried at 70° C. Product 29 is isolated in 27% yield as powder. M.p.29: >240° C.

Example 18

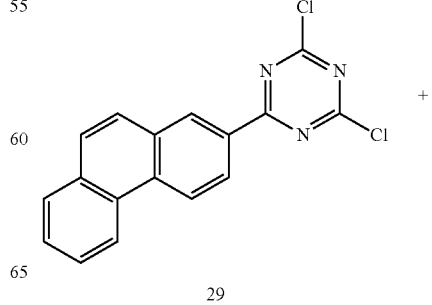

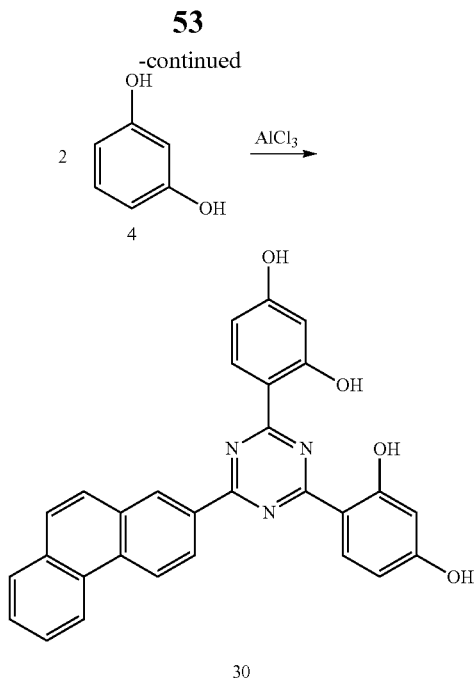

30

0.4 g (1.2 mmol) 29 is suspended in 3 ml chlorobenzene and 0.3 g (2.35 mmol) AlCl₃ is added. After 30 min stirring, 0.3 g (2.25 mmol) 4 is added and the reaction is heated up to 90° C. until all 29 is reacted. The reaction mass is cooled down to room temperature and the mass is quenched by addition of 10 ml 2N HCL. Product 30 is precipitated and filtered off. The crude product 30 is purified by column chromatography (silica gel, toluene/tetrahydrofuran as eluant) and obtained in 70% yield. M.p.30: >295° C.

Example 19

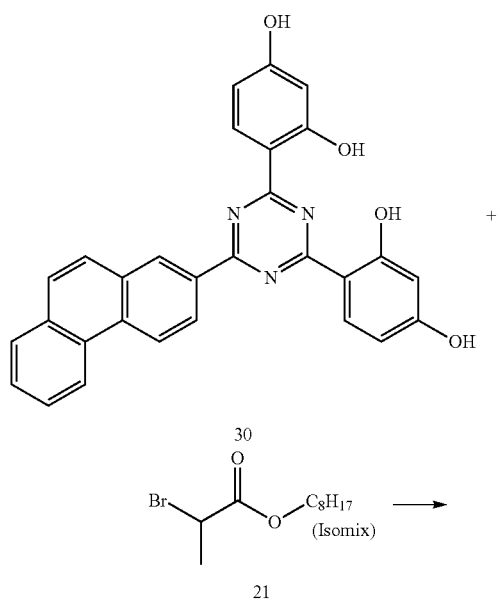

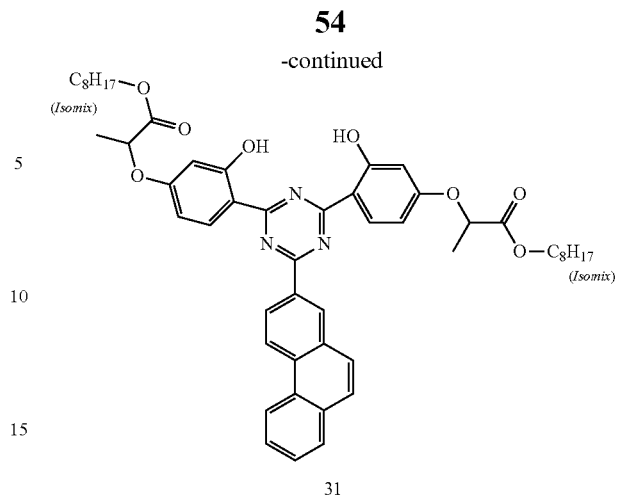

31

0.5 g (11 mmol) 30 and 0.18 g potassium carbonate are dissolved in 3 ml dimethyl-formamide. The solution is heated up to a temperature of 100° C. and then 0.35 g (1.3 mmol) 21 is added. The reaction mixture is kept at this temperature until all 30 is reacted and then cooled down to room temperature and hydrolyzed by addition of 20 ml water. The product is extracted by CH₂Cl₂. After distillation of the solvents, the crude product 31 is purified by column chromatography (silica gel, toluene, ethyl acetate as eluants) and obtained in 63% yield. UV/Vis (CHCl₃): $\lambda_{max}$: 308.5, 364, 400, 436.

Application Examples

Example 20

Photo Permanence

The photo permanence of the instant UV-absorbers is evaluated as follows:

The instant UV-absorbers are incorporated into a thermosetting acryl/melamine clear coat (based on Viacryl® SC 303/Viacryl® SC 370/Maprenal® MF 650) in a concentration of 3% based on the solids content of the formulation (solids content: 50.4%). The clear coat is sprayed onto glass plates resulting in a dry film thickness of the clear coat of 20 µm after cure (130° C./30 Min).

Prior to exposure of the specimens, the UV-absorption spectra are recorded using a UV/VIS spectrometer (Perkin Elmer, Lamda 40). Reference: unstabilized acryl/melamine clear coat. Subsequently the specimens are exposed in a Xenon—WOM weatherometer (Atlas Corp.) according to SAE J 1960. The percentage of UV-absorber retained (determined at λ max.) upon exposure is monitored by recording the UV-absorption spectra after regular exposure intervals. The test results are summarized in Table 1:

TABLE 1 photo permanence of claimed UV-absorbers during Xe-WOM exposure in comparison to commercial references

| | % UV-absorber retained after... hours Xe-WOM exposure | | | | |
|---|---|---|---|---|---|
| Sample | 1000 | 1500 | 2000 | 3000 | 4000 h |
| Compound of Example 9 | 100.0 | 100.0 | 97.4 | 85.1 | 76.4 |

TABLE 1-continued photo permanence of claimed UV-absorbers
during Xe-WOM exposure in
comparison to commercial references

| | % UV-absorber retained after . . . hours Xe-WOM exposure | | | | |
|---|---|---|---|---|---|
| Sample | 1000 | 1500 | 2000 | 3000 | 4000 h |
| Compound 9a of Example 4 | 100.0 | 89.3 | 83.7 | 78.8 | 73.7 |
| Compound 9b of Example 4 | 96.6 | 86.9 | 78.3 | 69.4 | 62.9 |
| hydroxy-phenyl-benzotriazole[1] | 68.3 | 50.8 | 40.2 | 18.7 | — |
| Hydroxy-phenyl-benzotriazole[2] | 83.0 | n.a. | 68.2 | 43.4 | 33.8 |
| hydroxy-phenyl-triazine[3] | 89.8 | 82.1 | 76.0 | 59.4 | 48.5 |
| Oxanilide[4] | 8 | — | — | — | — |

[1] TINUVIN ® 384
[2] TINUVIN ® 928
[3] TINUVIN ® 400
[4] SANDUVOR ® 3206

Example 21

In another example, two subsequent clear coats are applied on top of each other. The first clear coat (Clear coat I) is stabilized and applied as described in greater detail in Example 20. A second thermosetting acryl/melamine clear coat (based on Viacryl® SC 303/Viacryl® SC 370/Maprenal® MF 650) is subsequently sprayed onto the first clear coat resulting in a dry film thickness of the second clear coat (clear coat II) of 40 μm after cure (130° C./30 min). The second clear coat is stabilized using a UV-absorber combination of 3% TINUVIN® 109/1.5% TINUVIN® 400 and 1% TINUVIN® 152 as co-stabilizer (HALS). Reference: unstabilized first clear coat. As described in Example 20, the UV-transmission spectra are recorded prior to exposure of the specimens using a UV/VIS spectrometer (Perkin Elmer, Lamda 40). Subsequently the specimens are exposed in a Xenon—WOM wetherometer (Atlas Corp.) according to SAE J 1960. The transmission values (determined at 394 nm) as a function of the exposure period are monitored by recording the transmission spectra after regular exposure intervals. The test results are summarized in Table 2A and 2B.

Table 2A: transmission values (determined at 394 nm) as a function exposure intervals during Xe-WOM exposure

| | Transmission (%) after . . . hours | | | | | |
|---|---|---|---|---|---|---|
| Sample | initial | 500 | 1000 | 2000 | 3000 | 4000 |
| Clear coat I: unstabilized Clear coat II: 3% Tinuvin 109/1.5% Tinuvin 400 | 24.5 | 24.6 | 24.8 | 27.0 | 27.1 | 27.9 |
| Clear coat I: 3% compound of Example 9 Clear coat II: 3% Tinuvin 109/1.5% Tinuvin 400 | 0.18 | 0.2 | 0.22 | 0.24 | 0.25 | 0.31 |
| Clear coat I: 3% compound 9a of Example 4 Clear coat II: 3% Tinuvin 109/1.5% Tinuvin 400 | 0.15 | 0.26 | 0.29 | 0.33 | 0.41 | 0.51 |
| Clear coat I: 3% compound 9b of Example 4 Clear coat II: 3% Tinuvin 109/1.5% Tinuvin 400 | 0.01 | 0.65 | 0.79 | 0.95 | 1.28 | 1.52 |

TABLE 2B transmission values (determined at 388 nm) as a function
exposure intervals during Xe-WOM exposure

| | Transmission (%) after . . . hours | | | | | |
|---|---|---|---|---|---|---|
| Sample | initial | 500 | 1000 | 2000 | 3000 | 4000 |
| Clear coat I: 3% compound of Example 3 Clear coat II: 3% Tinuvin 109/1.5% Tinuvin 400 | 0.21 | 0.23 | 0.35 | 0.68 | 0.75 | 1.01 |

Example 22

Adhesion of Clear Coats Applied onto Electro Coats

As described in greater detail in Example 21, two subsequent clear coats layers are applied on top of electrocoated aluminum panels (ED 6950A, 10×30 cm) as commercially available from ACT Laboratories (ACT Laboratories, Inc., Southfield, Mich. 48 075, USA).

References: a) both clear coat layers unstabilized, b) second clear coat stabilized with existing UV-absorber package based on TINUVIN® 109/TINUVIN® 400, i.e. cutting out all UV-light in between 300-385 nm.

Subsequently the specimens are exposed in a Xenon—WOM weatherometer (Atlas Corp.) according to SAE J 1960. The adhesion between the clear coats and the light sensitive electro coat is determined at regular intervals by cross hatch (ISO 2409) followed by tape test. The test results are summarized in Table 3:

TABLE 3

| | Cross hatch value (ISO 2409 after . . . hours | | | |
|---|---|---|---|---|
| Sample | 250 h | 1000 h | 1500 h | 2000 h |
| Clear coat I/II; unstabilized | Gt 5 | — | — | — |
| Clear coat I: unstabilized clear coat II: 3% Tinuvin 109/1.5% Tinuvin 400 | Gt 0 | Gt 5 | — | — |
| Clear coat I: 3% compound of Example 9 Clear coat II: 3% Tinuvin 109/1.5% Tinuvin 400 | Gt 0 | Gt 0 | Gt 1 | Gt 2 |
| Clear coat I: 3% compound 9a of Example 4 Clear coat II: 3% Tinuvin 109/1.5% Tinuvin 400 | Gt 0 | Gt 0 | Gt 1 | Gt 2 |
| Clear coat I: 3% compound 9b of Example 4 Clear coat II: 3% Tinuvin 109/1.5% Tinuvin 400 | Gt 0 | Gt 1 | Gt 3 | — |
| Clear coat I: 3% compound of Example 3 Clear coat II: 3% Tinuvin 109/1.5% Tinuvin 400 | Gt 0 | Gt 0 | Gt 1 | — |

NOTE:
Gt 0 according to ISO 2409 = best (no loss of adhesion)
Gt 5 = worst (complete delamination)

Clearcoat Formulation:

|   | | |
|---|---|---|
| a) | Viacryl SC 303[1]<br>(65% solution in xylene/butanol, 26:9 wt./wt.) | 27.51 g |
| b) | Viacryl SC 370[2]<br>(75% in Solvesso 100[3]) | 23.34 g |
| c) | Maprenal MF 650[4]<br>(55% in isobutanol) | 27.29 g |
| d) | Butylacaetate/butanol (37:8 wt./wt.) | 4.33 g |
| e) | Isobutanol | 4.87 g |
| f) | Solvesso 150[5] | 2.72 g |
| g) | Crystal oil 30[6] | 8.74 g |
| h) | Baysilone MA[7] (1% in Solvesso 150) | 1.20 g |
| Total | | 100.00 g |

Raw materials:
[1]Viacryl SC 303: acrylic resin (Solutia, formerly Vianova Resins)
[2]Viacryl SC 370: acrylic resin (Solutia, formerly Vianova Resins)
[3]Solvesso 100: aromatic hydrocarbon, bp. 163-180° C. (Exxon Corp.)
[4]Maprenal MF 650: melamine resin (Solutia, formerly Vianova Resins)
[5]Solvesso 150: aromatic hydrocarbon, bp. 180-203° C. (Exxon Corp.)
[6]Crystal oil 30: aliphatic hydrocarbon, bp. 145-200° C. (Shell Corp.)
[7]Baysilone MA: leveling agent (Bayer AG)

The invention claimed is:
1. A composition stabilized against light-induced degradation which comprises
(a) an organic material subject to light-induced degradation, and
(b) a compound of formula (I) shown below

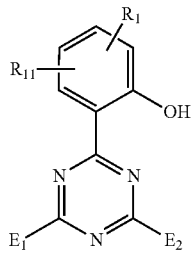

(I)

wherein
$E_1$ is a substituted or unsubstituted aromatic carbocyclic fused ring system comprising at least 3 rings;
$E_2$ is independently as defined for $E_1$; or is a substituted or unsubstituted naphthyl; or is a substituted or unsubstituted aromatic hetero ring system comprising one or more rings; or corresponds to the formula

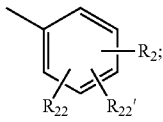

$R_1$ is H, $C_1$-$C_{24}$alkyl, $C_2$-$C_{18}$alkenyl, $C_5$-$C_{12}$cycloalkyl, $C_7$-$C_{15}$phenylalkyl, phenyl, or phenyl or said phenylalkyl substituted on the phenyl ring by $C_1$-$C_8$alkyl; or $OR_3$;
$R_2$ is H, $C_1$-$C_{18}$alkyl; $C_2$-$C_6$alkenyl; phenyl; phenyl substituted by $C_1$-$C_8$alkyl or by $C_1$-$C_8$alkoxy; $C_7$-$C_{11}$phenylalkyl; $C_5$-$C_{12}$cycloalkyl; $COOR_4$; CN; $NH_2$, $NHR_7$, $-N(R_7)(R_8)$, $NH-CO-R_5$; halogen; $C_1$-$C_{18}$haloalkyl; $C_1$-$C_{18}$alkoxy; $-S-R_3$ or $-O-R_3$;

$R_3$ is independently H, $C_1$-$C_{18}$alkyl; $C_5$-$C_{12}$cycloalkyl; $C_3$-$C_{18}$alkenyl; phenyl; $C_1$-$C_{18}$alkyl that is substituted by phenyl, OH, $C_1$-$C_{18}$alkoxy, $C_5$-$C_{12}$cycloalkoxy, $C_3$-$C_{18}$alkenyloxy, halogen, $-COOH$, $-COOR_4$, $-O-CO-R_5$, $-O-CO-O-R_6$, $-CO-NH_2$, $-CO-NHR_7$, $-CO-N(R_7)(R_8)$, CN, $NH_2$, $NHR_7$, $-N(R_7)(R_8)$, $-NH-CO-R_5$, phenoxy, $C_1$-$C_{18}$alkyl-substituted phenoxy, phenyl-$C_1$-$C_4$alkoxy, $C_6$-$C_{15}$bicycloalkoxy, $C_6$-$C_{15}$bicycloalkyl-alkoxy, $C_6$-$C_{15}$bicycloalkenyl-alkoxy and/or by $C_6$-$C_{15}$tricycloalkoxy; $C_5$-$C_{12}$cycloalkyl that is substituted by OH, $C_1$-$C_4$alkyl, $C_2$-$C_6$alkenyl and/or by $-O-CO-R_5$; $-CO-R_9$ or $-SO_2-R_{10}$; or $C_3$-$C_{50}$alkyl that is interrupted by one or more oxygen atoms and is unsubstituted or substituted by OH, phenoxy and/or by $C_7$-$C_{18}$alkylphenoxy; or -A; $-CH_2-CH(XA)-CH_2-O-R_{12}$; $-CR_{13}R_{13}'-(CH_2)_m-X-A$; $-CH_2-CH(OA)-R_{14}$; $-CH_2-CH(OH)-CH_2-XA$;

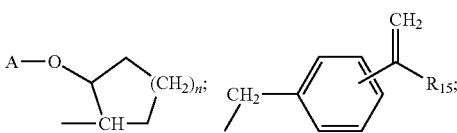

$-CR_{15}R_{15}'-C(=CH_2)-R_{15}"$; $-CR_{13}R_{13}'-(CH_2)_m-CO-X-A$;
$-CR_{13}R_{13}'-(CH_2)_m-CO-O-CR_{15}R_{15}'-C(=CH_2)-R_{15}"$ or $-CO-O-CR_{15}R_{15}'-C(=CH_2)-R_{15}"$;
A is $-CO-CR_{16}=CH-R_{17}$;
$R_4$ is independently $C_1$-$C_{18}$alkyl; $C_3$-$C_{18}$alkenyl; $C_7$-$C_{11}$phenylalkyl; $C_5$-$C_{12}$cycloalkyl; or $C_3$-$C_{50}$alkyl that is interrupted by one or more of $-O-$, $-NH-$, $-NR_7-$ and $-S-$ and is unsubstituted or substituted by OH, phenoxy and/or by $C_7$-$C_{18}$alkylphenoxy; or $C_2$-$C_{12}$hydroxyalkyl;
$R_5$ is independently H; $C_1$-$C_{18}$alkyl; $C_1$-$C_{18}$alkyl substituted by COOH or by $COOR_4$; $C_2$-$C_{18}$alkenyl; $C_2$-$C_{18}$alkenyl substituted by COOH or by $COOR_4$; $C_5$-$C_{12}$cycloalkyl; phenyl; $C_7$-$C_{11}$phenylalkyl; $C_6$-$C_{15}$bicycloalkyl; $C_6$-$C_{15}$bicycloalkenyl; or $C_6$-$C_{15}$tricycloalkyl;
$R_6$ is independently $C_1$-$C_{18}$alkyl; $C_3$-$C_{18}$alkenyl; phenyl; $C_7$-$C_{11}$ or $C_5$-$C_{12}$cycloalkyl;
$R_7$ and $R_8$ are independently $C_1$-$C_{12}$alkyl; $C_3$-$C_{12}$alkoxyalkyl; $C_4$-$C_{16}$dialkylaminoalkyl; or $C_5$-$C_{12}$cycloalkyl; or together form $C_3$-$C_9$-alkylene, -oxaalkylene or -azaalkylene;
$R_9$ is independently $C_1$-$C_{18}$alkyl; $C_2$-$C_{18}$alkenyl; phenyl; $C_5$-$C_{12}$cycloalkyl; $C_7$-$C_{11}$phenylalkyl; $C_6$-$C_{15}$bicycloalkyl, $C_6$-$C_{15}$bicycloalkyl-alkoxy, $C_6$-$C_{15}$bicycloalkenyl, or $C_6$-$C_{15}$tricycloalkyl;
$R_{10}$ is independently $C_1$-$C_{12}$alkyl; phenyl; naphthyl or $C_7$-$C_{14}$alkylphenyl;
$R_{11}$ and $R_{22}$ are independently H; $C_1$-$C_{18}$alkyl; $C_3$-$C_6$alkenyl; $C_5$-$C_{12}$cycloalkyl; phenyl; naphthyl; biphenylyl; $C_7$-$C_{11}$phenylalkyl; $C_7$-$C_{14}$alkylphenyl; halogen; $C_1$-$C_{18}$haloalkyl; or $C_1$-$C_{18}$alkoxy;
$R_{12}$ is independently $C_1$-$C_{18}$alkyl; $C_3$-$C_{18}$alkenyl; phenyl; phenyl substituted by one to three of the radicals $C_1$-$C_8$alkyl, $C_1$-$C_8$alkoxy, $C_3$-$C_8$alkenyloxy, halogen and trifluoromethyl; $C_7$-$C_{11}$-phenylalkyl; $C_5$-$C_{12}$cycloalkyl; $C_6$-$C_{15}$tricycloalkyl; $C_6$-$C_{15}$bicycloalkyl; $C_6$-$C_{15}$bicycloalkyl-alkyl;

$C_6$-$C_{15}$bicycloalkenyl-alkyl; —CO—$R_5$; or $C_3$-$C_{50}$alkyl that is interrupted by one or more of —O—, —NH—, —$NR_7$— and —S— and is unsubstituted or substituted by OH, phenoxy and/or by $C_7$-$C_{18}$alkylphenoxy;

$R_{13}$ and $R_{13}$' are independently H; $C_1$-$C_{18}$alkyl; or phenyl;

$R_{14}$ is independently $C_1$-$C_{18}$alkyl; $C_3$-$C_{12}$alkoxyalkyl; phenyl; or phenyl-$C_1$-$C_4$alkyl;

$R_{15}$, $R_{15}$' and $R_{15}$" are independently H or $CH_3$;

$R_{16}$ is independently H; —$CH_2$—COO—$R_4$; $C_1$-$C_4$alkyl; or CN;

$R_{17}$ is independently H; —$COOR_4$; $C_1$-$C_{17}$alkyl; or phenyl;

$R_{22}$' has one of the meanings of $R_{11}$; or is $NH_2$, $NHR_7$, NH—CO—$R_5$; —S—$R_3$, —$N(R_7)(R_8)$ or $OR_3$;

X is independently —NH—; —$NR_7$—; —O—; —NH—$(CH_2)_p$—NH—; or —O—$(CH_2)_q$—NH—;

and the indices are as follows:

m is a number from 0 to 19;
n is a number from 1 to 8;
p is a number from 0 to 4; and
q is a number from 2 to 4.

2. A composition according to claim 1 which comprises further additives.

3. A composition according to claim 2 which comprises as further additives phenolic and/or aminic antioxidants, sterically hindered amine stabilizers, UV-absorbers different from those of formula (I), phosphites, phosphonites, benzofuranones, metal stearates, metal oxides, pigments, dyes, organophosphorus compounds, hydroxylamines and/or flame retardants.

4. A composition according to claim 2 which comprises as further additives sterically hindered amine stabilizers and/or UV absorbers selected from the group consisting of the oxanilides, the hydroxybenzophenones, the benzoates, the α-cyanoacrylates, the benzotriazoles and the s-triazines different from those of formula (I).

5. A composition according to claim 1 wherein the organic material is a recording material.

6. A composition according to claim 1 wherein the organic material is a natural, semi-synthetic or synthetic polymer.

7. A composition according to claim 1 wherein the organic material is a coating composition.

8. A composition according to claim 7 wherein the coating composition is an automotive coating composition.

9. A composition according to claim 8 wherein the automotive coating comprises the following layers
d) a cathodically deposited coating, adhering to a metal substrate;
e) at least one subsequent coating layer containing a compound of formula (I) adhering to the cathodically deposited coating; and
f) a clear top coating containing one or more UV-absorbers different from those of formula (I) and optionally further lightstabilizers.

10. A composition according to claim 7 wherein the coating composition is applied onto a substrate, which is sensitive to electromagnetic radiation of wavelengths greater than 380 nm.

11. A composition according to claim 1, wherein the compound of formula (I) is present in an amount of from 0.1% to 30% by weight, based on the weight of the organic material.

12. A process for the stabilization of an organic material against the deleterious influence of UV and/or visible light, which comprises admixing and/or applying to said material as stabilizer a compound of formula (I) according to claim 1.

13. A process according to claim 12 wherein the organic material is a coating.

14. A process according to claim 13 wherein the coating is an automotive coating.

15. A process according to claim 12 wherein the organic material is an automotive coating, comprising
g) applying a cathodically deposited coating, adhering to a metal substrate;
h) incorporating into at least one coating adhering to the cathodically deposited coating a compound of formula (I); and
j) applying a clear top coating over the coating adhering to the cathodically deposited coating, which clear top coating contains one or more UV-absorbers different from those of formula (I) and optionally further lightstabilizers.

16. The composition according to claim 1, wherein $E_1$ is the formula

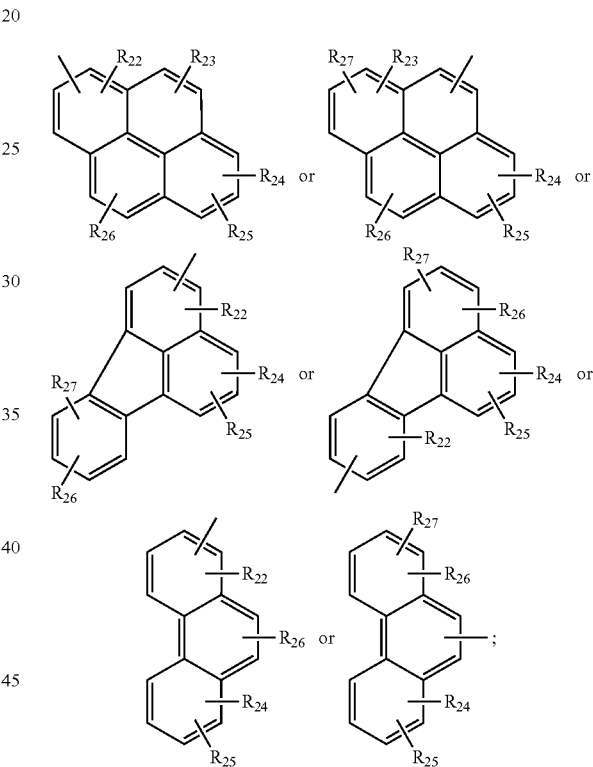

$E_2$ is independently as defined for $E_1$ or corresponds to the formula

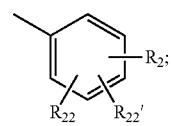

$R_{25}$ and $R_{27}$ are independently as defined for $R_{22}$;
$R_{23}$, $R_{24}$ and $R_{26}$ are independently as defined for $R_{22}$'.

17. The composition according to claim 1, wherein
$R_1$ is H, $C_1$-$C_{24}$alkyl, $C_2$-$C_{18}$alkenyl, $C_5$-$C_{12}$cycloalkyl, $C_7$-$C_{15}$phenylalkyl, phenyl, or said phenyl or said phenylalkyl substituted on the phenyl ring by $C_1$-$C_8$alkyl; or $OR_3$;

R$_2$ is H, C$_1$-C$_{18}$alkyl; C$_2$-C$_6$alkenyl; phenyl; phenyl substituted by C$_1$-C$_8$alkyl or by C$_1$-C$_8$alkoxy; NH—CO—R$_5$; halogen; C$_1$-C$_{18}$haloalkyl; C$_1$-C$_{18}$alkoxy; or OR$_3$;

R$_3$ is independently H, C$_1$-C$_{18}$alkyl; C$_5$-C$_{12}$cycloalkyl; C$_3$-C$_{18}$alkenyl; phenyl; C$_1$-C$_{18}$alkyl that is substituted by phenyl, OH, C$_1$-C$_{18}$alkoxy, C$_5$-C$_{12}$cycloalkoxy, C$_3$-C$_{18}$alkenyloxy, halogen, —COOH, —COOR$_4$, —O—CO—R$_5$, —O—CO—O—R$_6$, —CO—NH$_2$, —CO—NHR$_7$, —CO—N(R$_7$)(R$_8$), CN, NH$_2$, NHR$_7$, —N(R$_7$)(R$_8$), —NH—CO—R$_5$, phenoxy, C$_1$-C$_{18}$alkyl-substituted phenoxy and/or by phenyl-C$_1$-C$_4$alkoxy; C$_5$-C$_{12}$cycloalkyl that is substituted by OH, C$_1$-C$_4$alkyl, C$_2$-C$_6$alkenyl and/or by —O—CO—R$_5$; or —SO$_2$—R$_{10}$; or C$_3$-C$_{50}$alkyl that is interrupted by one or more oxygen atoms and is unsubstituted or substituted by OH, phenoxy and/or by C$_7$-C$_{18}$alkylphenoxy; or —CO—CH=CH$_2$ or —CO—C(CH$_3$)=CH$_2$;

R$_4$ is independently C$_1$-C$_{18}$alkyl; C$_3$-C$_{18}$alkenyl; C$_7$-C$_{11}$phenylalkyl; C$_5$-C$_{12}$cycloalkyl; or C$_3$-C$_{50}$alkyl that is interrupted by one or more of —O—, —NH—, —NR$_7$— and —S— and is unsubstituted or substituted by OH, phenoxy and/or by C$_7$-C$_{18}$alkylphenoxy; or C$_2$-C$_{12}$hydroxyalkyl;

R$_5$ is independently H; C$_1$-C$_{18}$alkyl; C$_2$-C$_{18}$alkenyl; C$_5$-C$_{12}$cycloalkyl; phenyl; or C$_7$-C$_{11}$phenylalkyl;

R$_6$ is independently C$_1$-C$_{18}$alkyl; C$_3$-C$_{18}$alkenyl; phenyl; C$_7$-C$_{11}$phenylalkyl; or C$_5$-C$_{12}$cycloalkyl;

R$_7$ and R$_8$ are independently C$_1$-C$_{12}$alkyl; C$_3$-C$_{12}$alkoxyalkyl; C$_4$-C$_{16}$dialkylaminoalkyl; or cyclohexyl; or together form C$_3$-C$_9$-alkylene or -oxaalkylene;

R$_{10}$ is independently C$_1$-C$_{12}$alkyl; phenyl; naphthyl or C$_7$-C$_{14}$alkylphenyl;

R$_{11}$ and R$_{22}$ are independently H, C$_7$-C$_{11}$phenylalkyl or C$_1$-C$_8$alkyl;

R$_{22}$' is independently H; C$_1$-C$_8$alkyl; C$_3$-C$_6$alkenyl; C$_7$-C$_{11}$phenylalkyl; C$_5$-C$_{12}$cycloalkyl; phenyl; naphthyl; biphenylyl; C$_7$-C$_{14}$alkylphenyl; NHR$_7$; —N(R$_7$)(R$_8$); halogen; C$_1$-C$_{18}$haloalkyl; or OR$_3$.

18. The composition according to claim 1, wherein

R$_1$ is H, C$_1$-C$_{24}$alkyl, C$_2$-C$_{18}$alkenyl, C$_5$-C$_{12}$cycloalkyl, C$_7$-C$_{15}$phenylalkyl, phenyl, or said phenyl or said phenylalkyl substituted on the phenyl ring by C$_1$-C$_8$alkyl; or OR$_3$;

R$_2$ is H, C$_1$-C$_8$alkyl; phenyl; phenyl substituted by methyl or by methoxy; NH—CO—R$_5$; tri-fluoromethyl; C$_1$-C$_{18}$alkoxy; or OR$_3$;

R$_3$ is independently H, C$_1$-C$_{18}$alkyl; cyclohexyl; C$_3$-C$_{18}$alkenyl; C$_1$-C$_{18}$alkyl that is substituted by phenyl, OH, C$_1$-C$_{18}$alkoxy, cyclohexyloxy, halogen, —COOH, —COOR$_4$, —O—CO—R$_5$, —CO—NHR$_7$, —CO—N(R$_7$)(R$_8$), CN, NHR$_7$, —N(R$_7$)(R$_8$), —NH—CO—R$_5$ and/or by phenyl-C$_1$-C$_4$alkoxy; or cyclohexyl that is substituted by OH, C$_1$-C$_4$alkyl, C$_2$-C$_6$alkenyl and/or by —O—CO—R$_5$;

R$_4$ is independently C$_1$-C$_{18}$alkyl; C$_7$-C$_{11}$phenylalkyl; C$_5$-C$_{12}$cycloalkyl; or C$_2$-C$_{12}$hydroxyalkyl;

R$_5$ is independently H; C$_1$-C$_{18}$alkyl; C$_2$-C$_8$alkenyl; cyclohexyl; phenyl; or C$_7$-C$_{11}$phenylalkyl;

R$_7$ and R$_8$ are independently C$_3$-C$_{12}$alkyl or cyclohexyl; or together form C$_3$-C$_9$oxaalkylene;

R$_{11}$ and R$_{22}$ are independently H, C$_7$-C$_{11}$phenylalkyl or C$_1$-C$_8$alkyl;

R$_{22}$' is independently H; C$_1$-C$_8$alkyl; C$_3$-C$_6$alkenyl; C$_7$-C$_{11}$phenylalkyl; C$_5$-C$_{12}$cycloalkyl; trifluoromethyl; phenyl; naphthyl; biphenylyl; C$_7$-C$_{14}$alkylphenyl; NHR$_7$; —N(R$_7$)(R$_8$); or OR$_3$.

19. The composition according to claim 16, wherein E$_1$' is the formula

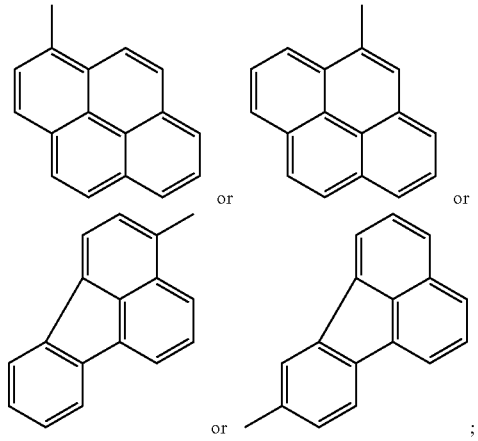

E$_2$' is independently as defined for E$_1$' or corresponds to the formula

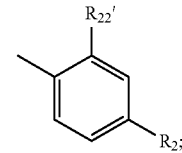

R$_1$ is H, C$_1$-C$_{12}$alkyl or OR$_3$;

R$_2$ is H, C$_1$-C$_8$alkyl; or OR$_3$;

R$_3$ is independently H, C$_1$-C$_{18}$alkyl; or C$_1$-C$_{12}$alkyl that is substituted by OH, C$_1$-C$_{18}$alkoxy, COOR$_4$ and/or by —O—CO—R$_5$;

R$_4$ is independently C$_1$-C$_{18}$alkyl;

R$_5$ is independently H; C$_1$-C$_{18}$alkyl; or C$_7$-C$_{11}$phenylalkyl;

R$_{11}$ is H; and

R$_{22}$' is H, methyl or OR$_3$.

\* \* \* \* \*